United States Patent
Meller et al.

(10) Patent No.: US 8,802,838 B2
(45) Date of Patent: Aug. 12, 2014

(54) ULTRA HIGH-THROUGHPUT OPTI-NANOPORE DNA READOUT PLATFORM

(75) Inventors: Amit Meller, Brookline, MA (US); Jerome Mathe, Somerville, MA (US); John S. Eid, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/173,247

(22) Filed: Jun. 30, 2011

(65) Prior Publication Data

US 2011/0257043 A1 Oct. 20, 2011

Related U.S. Application Data

(62) Division of application No. 11/573,627, filed as application No. PCT/US2005/028566 on Aug. 12, 2005, now Pat. No. 7,972,858.

(60) Provisional application No. 60/601,264, filed on Aug. 13, 2004.

(51) Int. Cl.
*C07H 21/04* (2006.01)
*C07H 19/00* (2006.01)
*C12Q 1/68* (2006.01)

(52) U.S. Cl.
USPC ......... 536/24.3; 536/22.1; 536/23.2; 435/6.1; 435/6.11

(58) Field of Classification Search
None
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,130,046 A | 10/2000 | Hubbell et al. | |
| 6,417,010 B1 | 7/2002 | Cargill et al. | |
| 6,528,258 B1 | 3/2003 | Russell | |
| 6,627,067 B1 * | 9/2003 | Branton et al. | 205/778 |
| 6,723,513 B2 | 4/2004 | Lexow | |
| 7,005,264 B2 | 2/2006 | Su et al. | |
| 7,972,858 B2 | 7/2011 | Meller et al. | |
| 2002/0028458 A1 * | 3/2002 | Lexow | 435/6 |
| 2002/0119455 A1 | 8/2002 | Chan | |
| 2003/0087253 A1 * | 5/2003 | Zhang et al. | 435/6 |
| 2003/0129611 A1 | 7/2003 | Bao et al. | |

(Continued)

FOREIGN PATENT DOCUMENTS

| | | |
|---|---|---|
| AU | 774389 | 6/2004 |
| CA | 2354635 | 7/2000 |

(Continued)

OTHER PUBLICATIONS

Tyagi et al. Nature Biotechnology. 1996. 14: 303-308.*

(Continued)

*Primary Examiner* — Robert T Crow
*Assistant Examiner* — Joseph G Dauner
(74) *Attorney, Agent, or Firm* — Wilmer Cutler Pickering Hale and Dorr LLP

(57) ABSTRACT

Described herein are methods for analyzing polymer molecules. These methods are employed for the high throughput readout of DNA and RNA molecules with single molecule sensitivity. The method of the present invention comprises (1) the electrically controlled unzipping of DNA (or RNA) double strands, and (2) the readout of the molecule's identity (or code) using one or more molecule signal detection.

26 Claims, 14 Drawing Sheets

(56) References Cited

U.S. PATENT DOCUMENTS

| | | | |
|---|---|---|---|
| 2004/0110179 A1* | 6/2004 | Shuber | 435/6 |
| 2006/0127940 A1 | 6/2006 | Bao et al. | |
| 2009/0029477 A1 | 1/2009 | Meller et al. | |

FOREIGN PATENT DOCUMENTS

| | | |
|---|---|---|
| CN | 1334879 | 2/2002 |
| EP | 1141399 | 10/2001 |
| EP | 1619259 | 1/2006 |
| EP | 1784754 | 5/2007 |
| JP | 2003-503007 | 1/2003 |
| WO | WO-01/81896 | 11/2001 |
| WO | WO-01/81908 | 11/2001 |
| WO | WO-02/42496 | 5/2002 |
| WO | WO03012119 A2 * | 2/2003 |
| WO | WO-2006/020775 | 2/2006 |

OTHER PUBLICATIONS

Deamer et al. TIBTech. 2000. 18: 147-151.*
Schimke. Phil Trans R Soc Lond. 1994. 345: 311-317.*
The Essentials of Molecular Biology. 3rd Edition.*
The Glossary of Biochemistry and Molecular Biology (Retrieved on Sep. 6, 2012 from the Internet: <URL: http://www.genscript.com/product_003/molecular_biology_glossary/id/606/category/glossary/concatenate_catenane_.html>).*
The Essentials of Molecular Biology. 3rd Edition. 1998.*
Akeson, M. et al., "Microsecond Time Scale Discrimination Among Polycytidylic Acid, Polyadenylic Acid, and Polyuridylic Acid as Homopolymers or as Segments within Single RNA Molecules," Biophys. J., 77, pp. 3227-3233, 1999.
Auld, et al., "A Neutral Amino Acid Change in Segment IIS4 Dramatically Alters the Gating Properties of the Voltage-Dependent Sodium Channel," Proc. Natl. Acad. Sci. USA, 87, pp. 323-327, 1990.
Bates et al., "Dynamics of DNA Molecules in a Membrane Channel Probed by Active Control Techniques," Biophys. J., 84, pp. 2366-2372, 2003.
Bonnet G, et al., "Thermodynamic Basis of the Enhanced Specificity of Structured DNA Probes," Proc. Natl. Acad. Sci., 96, pp. 6171-6176, 1999.
Dudko et al., "Extracting Kinetics from Single-Molecule Force Spectroscopy: Nanopore Unzipping of DNA Hairpins," Biophysical Journal, 92, pp. 4188-4195, 2007.
Ha et al., "Probing the Interaction between Two Single Molecules: Fluorescence Resonance Energy Transfer between a Single Donor and a Single Acceptor," Proc. Natl. Acad. Sci. USA, 93, pp. 6264-6268, 1996.
Hoshi, et al., "Biophysical and Molecular Mechanisms of Shaker Potassium Channel Inactivation," Science, 250, pp. 533-538, 1990.
Hoshi, et al., "Two Types of Inactivation in Shaker K+ Channels: Effects of Alterations in the Carboxy-Terminal Region," Neuron, 7, pp. 547-556, 1991.
Howorka et al., "Kinetics of Duplex Formation for Individual DNA Strands within a Single Protein Nanopore," PNAS USA, 98(23), pp. 12996-13001, 2001.
Howorka et al., "Sequence Specific Detection of Individual DNA Strands Using Engineered Nanopores," Nature Biotech, 19(7), pp. 636-639, 2001.
International Search Report and Written Opinion of the International Searching Authority, the United States Patent and Trademark Office, for International Application No. PCT/US2005/028566, dated Apr. 28, 2006, 4 pages.
Jegalian, "The Gene," Technology Review, 102(2), pp. 64-68, Mar./Apr. 1999.
Kasianowicz, et al., "Characterization of Individual Polynucleotide Molecules Using a Membrane Channel," Proc. Natl. Acad. Sci. USA, 93, pp. 13770-13773, 1996.

Kavarnos et al., "Photosensitization by Reversible Electron Transfer: Theories, Experimental Evidence, and Examples," Chem. Rev. 86, pp. 401-449, 1986.
Liphart, J. B. Onoa, S. B. Smith, I. Tinoco, Jr., and C. Bustamante, "Reversible Unfolding of Single RNA Molecules by Mechanical Force," Science; 292, pp. 733-737, 2001.
Lopez, et al., "Hydrophobic Substitution Mutations in the S4 Sequence Alter Voltage-Depending Gating in Shaker K+ Channels," Neuron, 7, pp. 327-336, 1991.
Mathe et al., "Orientation Discrimination of Single-Stranded DNA Inside the Alpha-Hemolysin Membrane Channel," Proc. Natl. Acad. Sci. USA, 102(35), pp. 12377-12382, 2005.
Mathe, J., H. Visram, V. Viasnoff, Y. Rabin, and A. Meller, "Nanopore Unzipping of Individual DNA Hairpin Molecules," Biophys. J., 87, pp. 3205-3212, 2004.
Mathis et al., "Steps Towards Spatially Resolved Single Molecule Detection in Solution," Bioimaging 5, pp. 116-128, 1997.
Meller, A., et al., "Rapid Nanopore Discrimination between Single Polynucleotide Molecules," Phys. Rev. Lett., 86, pp. 3435-3438, 2001.
Meller, et al., "Rapid Nanopore Discrimination Between Single Polynucleotide Molecules," Proc. Natl. Acad. Sci. USA, 97, pp. 1079-1084, 2000.
Meller, et al., "Single Molecule Measurements of DNA Transport Through a Nanopore," Electrophoresis, 23, pp. 2583-2591, 2002.
Milllar, "Time-resolved Fluorescence Spectroscopy," Curr. Opin. Struct. Biol., 6, pp. 637-642, 1996.
Muller et al., "Time-resolved Identification of Single Molecules in Solution with a Pulsed Semiconductor Diode Laser," Chem. Phys. Lett., 262, pp. 716-722, 1996.
Patton, et al., "Amino Acid Residues Required for Fast Na+-Channel Inactivation: Charge Neutrolizations and Deletions in the III-IV Linker," Proc. Natl. Acad. Sci. USA, 89, pp. 10905-10909, 1992.
Petit et al., "Assessment of Fluorochromes for Cellular Structure and Function Studies by Flow Cytometry," Biol. Cell, 78, p. 1-13, 15 pages, 1993.
Sauer et al., "Diode Laser Based Detection of Single Molecules in Solutions," Chem. Phys. Lett., 254, pp. 223-228, 1996.
Sauer-Budge, et al., "Unzipping Kinetics of Double-Stranded DNA in a Nanopore," Phys. Rev. Lett., 90, pp. 238101-1-238101-4, 2003.
Song, L., Hobaugh, M., Shustak, C., Cheley, S., Bayley, H. & Gouax, J., "Structure of Staphylococcal a-hemolysin a Heptameric Transmembrane Pore," Science, 274, pp. 1859-1865, 1996.
Supplementary European Search Report and Written Opinion of the European Patent Office for European Patent Application No. 05785616, dated Apr. 19, 2009, 6 pages.
Tyagi et al., "Molecular Beacons: Probes that Fluoresce Upon Hybridization," Nature Biotech. 14, pp. 303-308, 1996.
Vercoutere, W. A., S. Winters-Hilt, H. Olsen, D. Deamer, D. Haussler, and M. Akeson, "Rapid Discrimination Among Individual DNA Hairpin Molecules at Single-Nucleotide Resolution Using an Ion Channel," Nat. Biotechnol. 19, pp. 248-252, 2001.
Waggoner, "Covalent Labeling of Proteins and Nucleic Acids with Fluorophores," Methods Enzymol., 246, pp. 362-373, 1995.
West, et al., "A Cluster of Hydrophobic Amino Acid Residues Required for Fast Na+-Channel Inactivation," Proc. Natl. Acad. Sci. USA, 89, pp. 10910-10914, 1992.
Petit et al., "Assessment of Fluorochromes for Cellular Structure and Function Studies by Flow Cytometry," Biol. Cell, 78, p. 1, 1993.
Howorka et al., "Kinetics of Duplex Formation for Individual DNA Strands within a Single Protein Nanopore," PNAS USA, 98(23), pp. 12996, 2001.
Kavarnos et al., "Photosensitization by Reversible Electron Transfer: Theories, Experimental Evidence, and Examples," Chem. Rev. 86, pp. 401, 1986.
Milllar, "Time-resolved Fluorescence Spectroscopy," Curr. Opin. Struct. Biol., 6, pp. 637, 1996.
Muller et al., "Time-resolved Identification of Single Molecules in Solution with a Pulsed Semiconductor Diode Laser," Chem. Phys. Lett., 262, pp. 716, 1996.

* cited by examiner (a)

(b)

SEQUENCE LISTING

<160> NUMBER OF SEQ ID NOS: 20

<210> SEQ ID NO 1
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctctgttgc tctctcgcaa cagagcaaaa aaaaaaaaaa aaaaaaaaaa aaaaaaaaaa      60
aaaaaaaaaa aaaaaa                                                      76

<210> SEQ ID NO 2
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gctctgttgc tctctcgcaa ctgagcaaaa aaaaaaaaaa aaaaaaaaaa aaaaaaaaaa      60
aaaaaaaaaa aaaaaa                                                      76

<210> SEQ ID NO 3
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcgaacttt tgttcgacaa aaaaaaaaaa aaaaaaaaaa aaaaaaaaaa aaaaaaaaaa      60
aaaaaaaa                                                               68

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atttattagg                                                             10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cctaataaat                                                             10

<210> SEQ ID NO 6
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 6
cggcgggcaa                                                            10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttgcccgccg                                                            10

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtagccccag cagtccaggg t                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
accctggact gctggggcta c                                               21

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gccccagcag tccagggt                                                   18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
accctggact gctggggc                                                   18

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 12
ccagcagtcc agggt                                                          15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
accctggact gctgg                                                          15

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcagtccagg gt                                                             12

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
accctggact gc                                                             12

<210> SEQ ID NO 16
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 gtccagggt                                                                  9

<210> SEQ ID NO 17
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 accctggac                                                                  9

<210> SEQ ID NO 18
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 18
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa                                       90

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaaaaaaaa aaaaaaaaaa aaaaaaaaaa aaaaaaaaaa aaaaaaaaaa                 50

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttgccgcccg                                                             10
```

ULTRA HIGH-THROUGHPUT OPTI-NANOPORE DNA READOUT PLATFORM

RELATED APPLICATIONS

This application is a division of U.S. patent application Ser. No. 11/573,627, accorded a 35 U.S.C. §371(c) date of Aug. 21, 2008, which is a national phase filing under 35 U.S.C. §371 of international application number PCT/US2005/028566, filed Aug. 12, 2005, which claims the benefit of priority to U.S. Provisional Patent Application No. 60/601,264, filed Aug. 13, 2004, the disclosures of all of which are incorporated by reference herein.

SEQUENCE LISTING

The instant application contains a Sequence Listing which has been submitted in ASCII format via EFS-Web and is hereby incorporated by reference in its entirety. Said ASCII copy, created on Jan. 31, 2012, is named 42697240.txt and is 5,405 bytes in size.

STATEMENT OF FEDERAL GOVERNMENTAL SUPPORT

This invention was made with government support under grant HG003574 awarded by National Institutes of Health. The government may have certain rights in the invention.

FIELD OF INVENTION

The present invention provides a system for analyzing polymer molecules. In particular, the instant invention is directed to single-stranded polynucleotide molecule sequencing.

BACKGROUND

Ever since Watson and Crick elucidated the structure of the DNA molecule in 1953, genetic researchers have wanted to find fast and efficient ways of sequencing individual DNA molecules. Sanger/Barrell and Maxam/Gilbert developed two new methods for DNA sequencing between 1975 and 1977, which represented a major breakthrough in sequencing technology. All methods in extensive use today are based on the Sanger/Barrell method and developments in DNA sequencing in the last 23 years have more or less been modifications of this method.

Polynucleotides are polymeric molecules comprising repeating units of nucleotides bound together in a linear fashion. Examples of polynucleotides are deoxyribonucleic acid (DNA) and ribonucleic acid (RNA). DNA polymers are made up of strings of four different nucleotide bases known as adenine (A), guanine (G), cytosine (C), and thymine (T). The particular order, or "sequence" of these bases in a given gene determines the structure of the protein encoded by the gene. Furthermore, the sequence of bases surrounding the gene typically contains information about how often the particular protein should be made, in which cell types, etc. Knowledge of the DNA sequence in and around a gene provides valuable information about the structure and function of the gene, the protein it encodes, and its relationship to other genes and proteins. RNA is structurally and chemically related to DNA, however, the sugar component of RNA is ribose (as opposed to DNA which is deoxyribose) and the base thymine is substituted with uracil.

It is appreciated by those skilled in the art that there is a direct relationship between particular DNA sequences and certain-disease states. This fact has encouraged many pharmaceutical companies to invest heavily in the field of genomic research in the hope of discovering the underlying genetic nature of these diseases.

Another reason that sequence information is important is the expected ability to determine an individual's susceptibility to particular diseases based on his or her genetic sequence. The field of genetic diagnostics is dedicated to identifying nucleotide sequence elements whose presence in a genome correlates with development of a particular disorder or feature. The more information is available about genomic sequence elements observed in the population the more powerful this field becomes. Furthermore, the more rapidly information about the prevalence and penetrance of sequence elements in the general population, as well as the presence of such elements in the genomes of particular individuals being tested, the more effective the analysis becomes.

Yet another reason that sequence information is valuable is that a number of pharmaceutical companies seek to develop drugs that are custom-tailored to an individual's genetic profile. The hope is to provide targeted, potent drugs, possibly with decreased dosage levels appropriate to the genetic characteristics of the particular individual to whom the drug is being administered.

Most currently available nucleotide sequencing technologies determine the nucleotide sequence of a given polynucleotide strand by generating a collection of complementary strands of different lengths, so that the collection includes molecules terminating at each base of the target sequence and ranging in size from just a few nucleotides to the full length of the target molecule. The target molecule's sequence is then determined by analyzing the truncated complementary strands and determining which terminate with each of four DNA nucleotides. A "ladder" is constructed by arranging the truncated molecules in order by length, and the terminal residue of each rung is read off to provide the complement of the target polynucleotide sequence.

Currently available DNA sequencing systems are very powerful. However, they are limited by their speed, their complexity, and their cost. The speed of currently available automated sequencers is limited by the inability of the machines to analyze more than several hundred (typically around 600) nucleotides of sequence at a time. Allowing for the overlaps needed to piece together correctly strands less than 1000 bases longs, the standard sequencing process has to be performed as many as 70 million times in order to determine the human genome sequence (Technology Review 102 (2):64-68 1999 March/April; incorporated herein by reference). At a theoretical rate of even 100 million bases per day it will take at least a year to sequence the human genome once. With these techniques, large-scale sequencing cannot become a clinical tool. For genetic diagnostics to become practical in a clinical setting, the sequencing rate will have to be increased by at least three to five orders of magnitude.

The complexity of current sequencing technology arises from the need to amplify and modify the genetic molecules being sequenced. This modification is carried out either chemically or enzymatically, and amplification is achieved by numerous cycles of heating and cooling. One of the more popular ways of amplifying and modifying the DNA to be sequenced is using the polymerase chain reaction (PCR). PCR involves successive rounds of denaturing, annealing, and extension using a DNA polymerase and resulting in the exponential amplification of the original strand of DNA. The length of time associated with each part of the cycle depends on the fluid volume and the length of DNA to be amplified. Typical times are on the order of 10-30 seconds for the denaturation step, 5-30 seconds for the annealing step, and 1-4 minutes for the extension step. This cycle is usually carried out 15 to 30 times. Therefore, normal PCR times are one-to three hours depending on the length of the DNA to be amplified. The fundamental physical processes that constrain the denaturing, annealing, and labeling are the number of detectable strands needed, the time needed to carry out this process, and the processivity of the enzyme. This entire process is time consuming and requires following involved procedures.

Currently there is a need for a more efficient method for sequencing polynucleotides. The present invention provides for such a method.

SUMMARY

The present invention is directed towards methods for analyzing polymer molecules. These methods are employed for the high throughput readout of DNA and RNA molecules with single molecule sensitivity. The method of the present invention comprises (1) the electrically controlled unzipping of DNA (or RNA) double strands, (2) the readout of the molecule's identity (or code) using one or more molecule signal detection, and (3) a controlled slowing down of the nanopore threading process by virtue of the molecular interactions between the nucleic acid and hybridized probes (e.g., strongly interacting probes result in further decrease in translocation velocity).

The instant invention is directed to a sequencing method that involves the conversion of a target polynucleotide, such as DNA, into a designed polynucleotide polymer (or simply "Design Polymer"). This Design Polymer is encoded by a binary code which is read by a detector, thus providing sequence information reflecting the original target polynucleotide.

In one embodiment of the present invention, a target double-stranded polynucleotide is converted into a Design Polymer. In one aspect, a single-strand of the target is processed. The conversion involves the replacement of each nucleotide base of the target polynucleotide with two Design Monomers thereby representing that base as a binary code. For example, the base adenine can be represented by 0+0, the base cytosine by 0+1, the base guanine by 1+0, and the base thymine by 1+1. In a particular aspect, each Design Monomer is a double-stranded polynucleotide sequence. Each of the Design Monomers represents either a "0" or a "1." Hence, for each and every base of the target polynucleotide, there are two corresponding double-stranded Design Monomers. In one aspect, the Design Monomers are ligated in such a manner so as to reflect the nucleotide sequence of the target polynucleotide, thus forming a Design Polymer. In one aspect, the double-stranded Design Polymer is converted to a single-stranded molecule. The single-stranded Design Polymer is hybridized with appropriate molecular beacons, wherein each molecular beacon comprises one or more signal molecules and one or more quencher molecules.

In one aspect of the present invention, the Design Polymer comprises only two sets of Design Monomers: (1) one set of Design Monomers code for "0," and (2) the other set of Design Monomers code for "1." In a particular aspect of the invention, only two sets of molecular beacons are employed. One set of molecular beacons hybridizes to Design Monomers representing "0," whereas the second set of molecular beacons hybridizes to Design Monomers representing "1." In one aspect, the two sets of molecular beacons comprise unique signal molecules, such that molecular beacons that hybridize to "0" Design Monomers have a different signal molecule than the molecular beacons that hybridize to "1" Design Monomers. The hybridization of molecular beacons to individual Design Monomers of the Design Polymer forms a Beacon-Design Polymer Complex (or simply, "BDP complex").

In one aspect of the instant invention, the molecular beacons comprise suitable fluorophores as signal molecules. In another aspect, the molecular beacon comprises not only a fluorophore but a quencher as well. In a particular aspect, a fluorophore is located at the 5' end of the beacon, whereas the quencher is located at its 3' end.

Methods of the present invention employ electrically driven unzipping of double helical nucleic acids. By using an electrically driven nanopore unzipping method, control over the unzipping time can be maintained, permitting the use of, for example, self-quenched fluorescence probes, such as the widely used molecular beacons. Advantageously, different measurement schemes can be used in which the fluorescence probes are quenched until the moment of their readout set by the unzipping event.

One embodiment of the invention is directed to a nanopore system. In one aspect, the nanopore comprises α-Hemolysin. The nanopore of the present invention can be used to obtain sequence information of a polynucleotide. The BDP complex can be introduced to the nanopore of the present invention. In one aspect, there is a 3' overhang of the Design Polymer (of the BDP complex) that is introduced into the nanopore of the present invention. This 3' overhang sequence can penetrate through the nanopore until the double-stranded part of the BDP complex is in apposition with the entry pore. The dimension of the nanopore is such that only single-stranded polynucleotides can penetrate, thus the double-stranded BDP complex is precluded from entry. A voltage can be applied across the nanopore to unzip the double-stranded BDP complex. This unzipping of the double strand facilitates the removal of a molecular beacon from the Design Polymer, thus permitting a signal molecule, e.g., a fluorophore, to elaborate its signal, such as luminescence. Additionally, the unzipping permits entry of the single-stranded Design Polymer into and through the nanopore. The signal can be detected by a suitable detector. After a suitable time, the released molecular beacon will self-hybridize thereby quenching its own signal.

This a reiterative process, the applied voltage continues to translocate the unzipped single-stranded Design Polymer through the pore until the next portion of the single-stranded Design Polymer is completely through whereupon a subsequent signal from the next molecular beacon in sequence is elaborated registering another signal by a suitable detector, and is then self-quenched when it is released from the BDP complex. In this manner the entire Designed Polymer can be read.

The present invention also pertains to an optical system that can be used with single-molecule detection. This optical system can be used in conjunction with one or more nanopore systems. The present optical system comprises a custom made flow cell having a nanopore support and two electrodes. The electrodes are used to apply an electric field required for the unzipping process while the support enables the suspension of a phospholipid bilayer in the proximity of a glass coverslip thereby enabling imaging of the bilayer using a high-power microscope objective. The flow cell is mounted on an XYZ nanopositioner in an inverted microscope and can be mobilized for precision alignment with the optical axis using a translation stage.

In the following description of certain embodiments, reference is made to the accompanying drawings, which form a part hereof, and in which is shown by way of illustration a specific embodiment in which the invention can be practiced. It is to be understood that other embodiments can be utilized and structural changes can be made without departing from the scope of the present invention. In the case of any structures, it is to be understood that these figures are somewhat simplified because they do not show all conventional details of the depicted structures, but only the relevant elements. In addition, while a particular embodiment is shown here, this is not intended to be limiting.

DETAILED DESCRIPTION

The present invention is directed towards methods for analyzing polymer molecules. These methods are employed for the high throughput readout of DNA and RNA molecules with single molecule sensitivity. The method of the present invention comprises (1) the electrically controlled unzipping of DNA (or RNA) double strands, (2) the readout of the molecule's identity (or code) using one or more molecule signal detection, and (3) a controlled slowing down of the nanopore threading process by virtue of the molecular interactions between the nucleic acid and hybridized probes (e.g., strongly interacting probes result in further decrease in translocation velocity).

Described herein is the employment of two single-molecule detection methods: (1) nanopore detection, and (2) single-molecule signal probing, such as fluorescence probing. Double-stranded polynucleotides, such as double helix DNA, can be unzipped using an active control of an applied electric field over a nanopore. This unzipping of the double-stranded polynucleotide produces single-stranded elements that can pass through a channel of the nanopore, while double-stranded portions are precluded from entry. The entry of the single-stranded elements of the polynucleotide thus facilitates its analysis, such as obtaining sequence information.

The methods of the present invention involve the conversion of a target polynucleotide molecule into a binary code Design Polymer. A target polynucleotide can be obtained from any source. In one aspect, the target polynucleotide can be a double-stranded polynucleotide molecule such as a double helix DNA. Other polynucleotides are also within the scope of this invention including, but not limited to, RNA and PNA molecules. The target polynucleotide can be single stranded. The target molecule can comprise both natural and modified nucleotide bases. The target can be of any origin. For example, the target can be cDNA or gDNA or man-made (synthesized) sequence used to encode any information in an ultra high density format. The target polynucleotide can be partially or completely synthesized. The target can comprise nucleotides of natural origin including both plant and animal. The target polynucleotide can be of any length. For example, the range in size can be from about 10 nucleotide bases to about 100 thousand or greater nucleotide bases.

Figure 1:
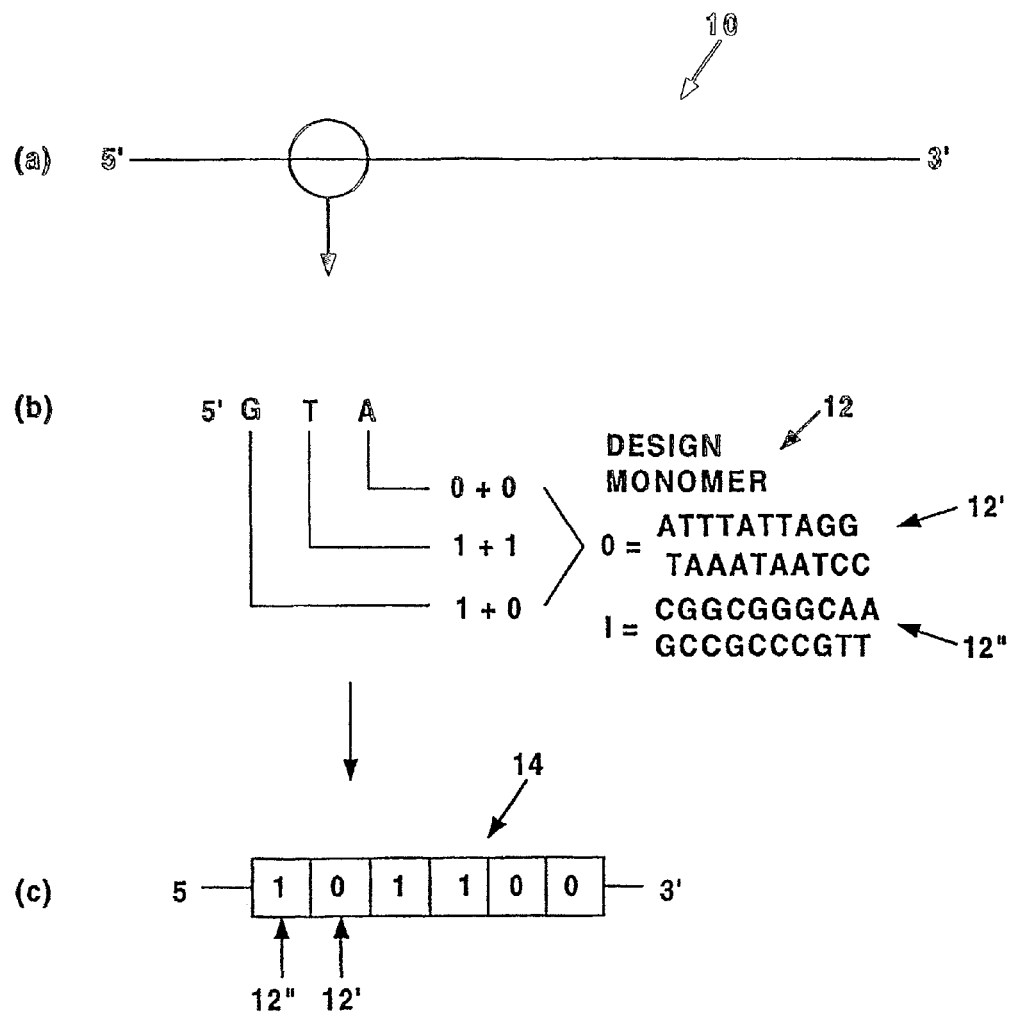
FIG. 1 is a schematic representation of the conversion of a target polynucleotide to a Design Polymer where (a) is the target polynucleotide, (b) is an isolated portion of the target (SEQ ID NOS 4-7, respectively, in order of appearance), and (c) is the resulting Design Polymer.

Referring to FIG. 1, a target polynucleotide 10 is obtained (FIG. 1a). This target polynucleotide 10 is subjected to biochemical conversion. See, U.S. Pat. No. 6,723,513 to Lexow, the entire teaching of which is incorporated herein by reference. For example, three nucleotides have been isolated from the target polynucleotide for illustrative purposes (FIG. 1b). The three nucleotides are "G," "T," and "A" (guanine, thymine, and adenine, respectively). The conversion process will be described using just these three nucleotides.

In this conversion process, each nucleotide is represented by a binary code using "1" and "0." So, for example, guanine (G) can be represented by the binary code "1+0", thymine (T) by "1+1", adenine (A) by "0+0", and cytosine (C) by "0+1". The "1" and "0" of the binary code are represented by their own unique polynucleotide referred to as a "Design Monomer" 12. See, FIG. 1b. FIG. 1b provides an example of such Design Monomers 12. What is depicted in FIG. 1b is a Design Monomer 12' for "0" and a Design Monomer 12" for "1". (The precise polynucleotide sequence for a Design Monomer can be determined by a practitioner.) Therefore, because the Design Polymer 12 comprises a binary code there are two Design Monomers 12', 12" each representing either "1" or "0" but not simultaneously both "1" and "0".

In the example provided in FIG. 1, there is a Design Monomer 12' for "0" and a Design Monomer 12" for "1". Given that each nucleotide is represented by a binary code necessitates that each nucleotide is represented by two Design Monomers. For example, guanine is represented by the binary code "1+0", therefore, guanine is represented by the Design Monomer 12" for "1" and by the Design Monomer 12' for "0". However, the Design Monomers must be in proper sequence in order to reflect the particular nucleotide they are representing. So for guanine, Design Monomer 12" "1" must be followed by Design Monomer 12' "0" (using the conventional map assignment of 5'→3').

A Design Polymer 14 comprises Design Monomers 12', 12" arrayed in a particular sequence. See, FIG. 1c. The Design Polymer's 14 sequence reflects the nucleotide sequence of the original target polynucleotide 10 in that the Design Monomers 12', 12" are arranged from 5' to 3' in the same order found by their cognate nucleotides in the original target polynucleotide 10.

The process presented in FIG. 1 can be repeated for an entire polynucleotide molecule. The size of a target polynucleotide can be manipulated for convenience, however, the principles remain the same.

A Design Monomer of the present invention comprises a polynucleotide molecule. The size of the Design Monomer can vary. In one aspect, the size of the Design Monomer can range from about ten (10) nucleotides to about one hundred (100) nucleotides. In another aspect, the Design Monomer is a double-stranded polynucleotide. The polynucleotide can be DNA, RNA or PNA. The nucleotide constituents of a Design Monomer can be natural, modified, or a combination thereof. They can be selected from the group consisting of adenine, cytosine, guanine, thymine, uracil, modifications thereof, and alike. A practitioner can construct Design Monomers based on the parameters of a given protocol. The key is that at least two different Design Monomers should be constructed in order to effectuate the binary code feature of the present invention.

A Design Polymer of the present invention comprises a plurality of Design Monomers. The Design Polymer represents a biochemically converted target polynucleotide. The relationship between the Design Polymer and the original target polynucleotide is such that a practitioner can, using only the Design Polymer, determine the nucleotide sequence of the original target polynucleotide. The Design Monomers of a Design Polymer are linked together, for example, covalently linked, to form a polynucleotide molecule. Again, the sequence of linking the Design Monomers is such that their linkage sequence reflects the original sequence of nucleotides in the target.

Hybrid systems are also within the scope of the present invention. For example, if the target polynucleotide is an RNA molecule, the Design Monomers used to construct the binary code can comprise deoxyribonucleotides. The converse is equally valid. If a practitioner desires, there can be hybrid constructs. For example, a Design Monomer(s) can comprise a hybrid of deoxyribonucleotides and ribonucleotides. Various hybrid permutations are well within the scope of this invention.

Figure 2:
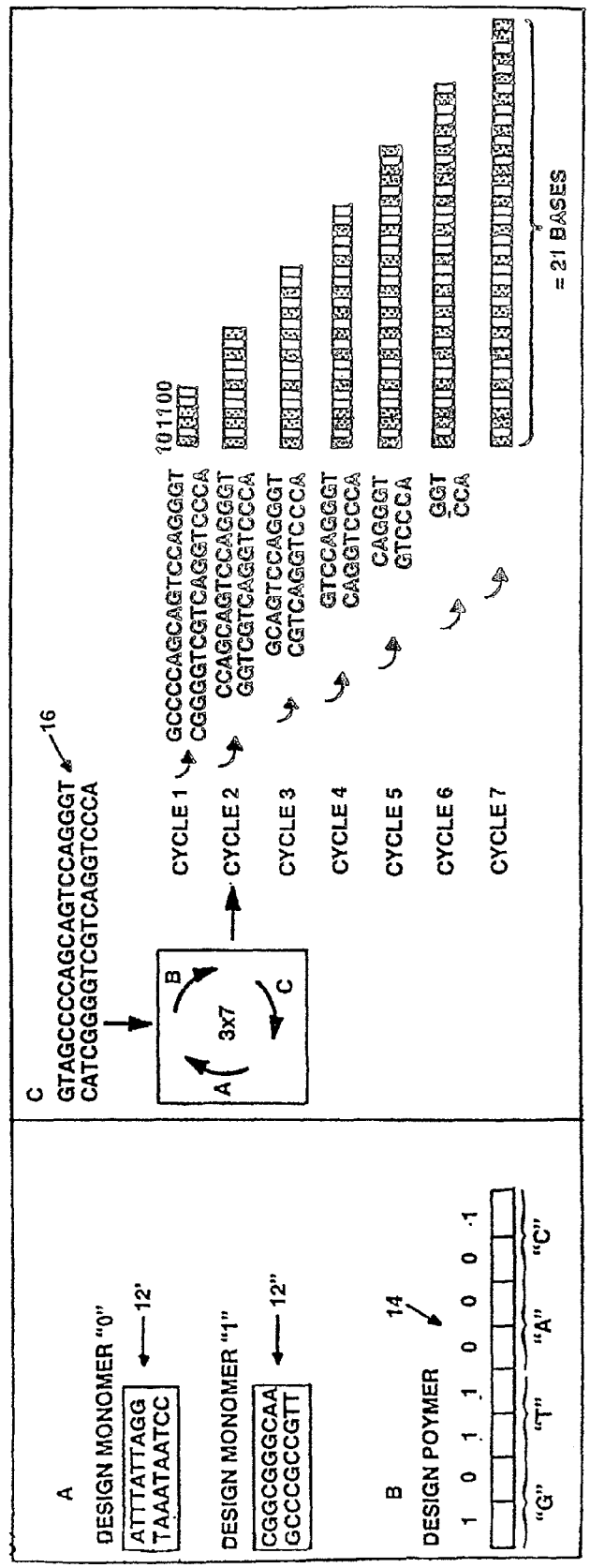
FIG. 2 is a schematic representation of the cycles involved in the conversion of a target polynucleotide to a Design Polymer where (a) are two Design Monomers (SEQ ID NOS 4-6 and 20, respectively, in order of appearance), (b) is the Design Polymer, and (c) illustrates the cycles involved in converting the target (SEQ ID NOS 8-17, respectively, in order of appearance).

Referring to FIG. 2, polynucleotides and oligonucleotides (differing only relative to size) can be processed according to the method described above. The method described in FIG. 1 can be a reiterative process, thus permitting an oligomer to under conversion into a Design Polymer. FIG. 2 depicts such a scenario. For this example, an oligomer 16 of 21 base pairs is being used to illustrate the method. Oligomers of various sizes are within the scope of the present invention. For example, oligonucleotides ranging from about 10 nucleotides to about 5000 nucleotides can be processed. As previously stated, polynucleotides of considerable length can be digested forming shorter oligonucleotides using conventional methods well known to those skilled in the art.

FIG. 2a depicts two Design Monomers, one 12' represents "0" and the other 12" represents "1". Upon closer examination it can be observed that the two Design Monomers 12', 12" comprise different nucleotide sequences. In this particular example, each Design Monomer comprises ten base pairs. These two Design Monomers 12', 12" can now be used to represent the target nucleotide 16 sequence via a binary code. FIG. 2b illustrates the binary code assignment, also, FIG. 2b depicts a Design Polymer 14 formed by linking Design Monomers 12', 12" together. The length and sequence of the Design Monomers 12', 12" is flexible which permits the resulting Design Polymer 14 to be tailored made.

FIG. 2c illustrates the conversion cycling of target to Design Polymers. The target polynucleotide 16 can be cycled through three enzymatic steps: A, B, and C. In this illustration, three target bases are converted per cycle. The target polynucleotide 16 in this illustration comprises 21 base pairs, therefore, a total of seven cycles is required for full conversion the target. In FIG. 2c, the upper strand (bold) is converted in this illustration.

Enzymatic step A comprises the digestion of the target 16 with at least two IIs restriction enzymes, such as NlaIII, in order to generate overhangs for conversion and Design Polymer linkage. It is well appreciated by those skilled in the art that digestion of a target polynucleotide can be accomplished employing other restriction enzymes known in the art.

Step B is a litigation step where binary Design Polymer sequences are specifically attached to the 3' ends of target fragments having the corresponding sequence in the 5' end. This step involves the division of target fragments into separate wells where the number of wells corresponds to the number of permutations of bases being converted (e.g., conversion of three bases requires 64 wells). In each well there is a Design Polymer sequence and a specific adapter (not shown) corresponding to the sequence that should be converted in that particular well (i.e., there will be a non-specific association of the Design Polymer to the 3' end of each fragment and a specific ligation of the adapter to the 5' end of the correct fragments). Following ligation, the wells can be pooled into one containing vessel.

Step C is an amplification step. A polymerase chain reaction (PCR) step is performed to amplify and select those fragments that have successfully been attached to a Design Polymer and a specific adapter.

This conversion method can be performed with massive parallelism where billions of different target molecules are converted in the same reaction. See, U.S. Pat. No. 6,723,513.

Once the Design Polymer is formed, one or more signal molecules are associated with the Design Polymer. In one aspect, the signal molecule is a molecular beacon. A single-stranded Design Polymer is obtained through means well known to those skilled in the art. The single-stranded Design Polymer is admixed with molecular beacons under conditions suitable for hybridization (e.g., by slow temperature quenching in the following buffer 100 mM KCl, 1 mM $MgCl_2$ 10 mM Tris-Hcl, pH 8.0) forming a Beacon-Design Polymer complex (BDP complex).

Figure 3:
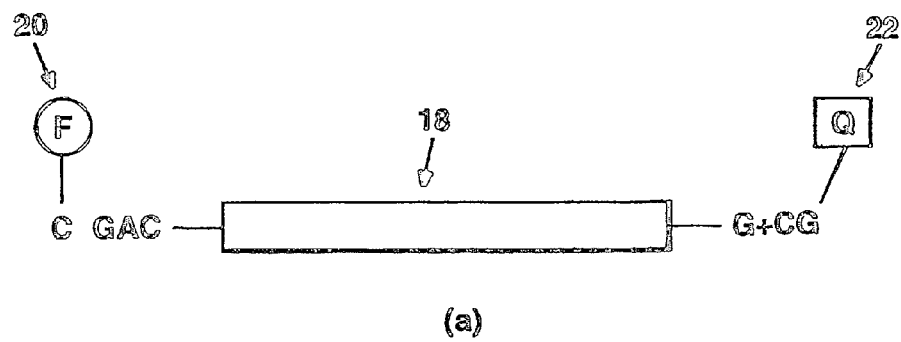
FIG. 3 is a schematic representation of a molecular beacon where (a) is a linearized representation of the beacon, and (b) represents the beacon self-hybridized.
Figure 3:
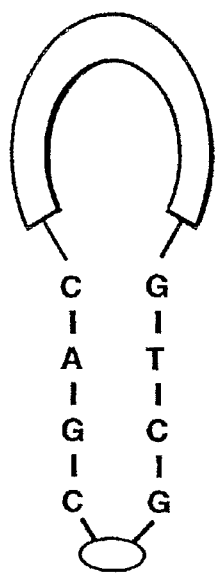

FIG. 3 depicts schematically a typical molecular beacon 18. (See, Tyagi S, Kramer FR. 1996 Molecular beacons: Probes that fluoresce upon hybridization, *Nature Biotech.* 14:303-8; Bonnet G, Tyagi S, Libchaber A, and Kramer FR. 1999. Thermodynamic basis of the enhanced specificity of structured DNA probes. *Proc. Natl. Acad. Sci.* 96:6171-76). A molecular beacon (or simply "beacon") is an oligonucleotide that has a fluorophore ("F") 20 at one position of the oligonucleotide, e.g., the 5' end and a quencher ("Q") 22 at another position of the oligonucleotide, e.g., the 3' end. See, FIG. 3a. As depicted in FIG. 3a, the fluorophore 20 can emit a fluorescence signal because it is not encumbered by the quencher 22. However, the 5' end and the 3' end of a beacon 18 can self-hybridize due to having complementary bases. See, FIG. 3b. When the 5' and 3' end hybridize or are in close approximation the quencher 22 will quench the fluorophore 20, thus preventing the signal to be elaborated.

In the methods of the present invention, at least two different molecular beacons are employed. One molecular beacon will hybridize to Design Monomers representing "0", while another molecular beacon will hybridize to Design Monomers representing "1". Molecular beacons hybridizing to Design Monomer "0" will comprise a signal, such as a fluorophore, that is different from a molecular beacon that hybridizes to Design Monomer "1". For example, molecular beacon "0" (i.e., a molecular beacon hybridizing to a Design Monomer "0") can have fluorophore "F0" and molecular beacon "1" can have fluorophore "F1" both of which emit a different and discernable signal.

In one aspect, the percent hybridization between a beacon and a Design Monomer is about 90% or greater. In another aspect, the percent hybridization of a beacon to a Design Monomer is from about 80% to about 90%. In yet another aspect, the percent hybridization of a beacon to a Design Monomer is about 70% to about 80%. In a further aspect, the percent hybridization of a beacon to a Design Monomer is from about 60% to about 70%.

Figure 4:
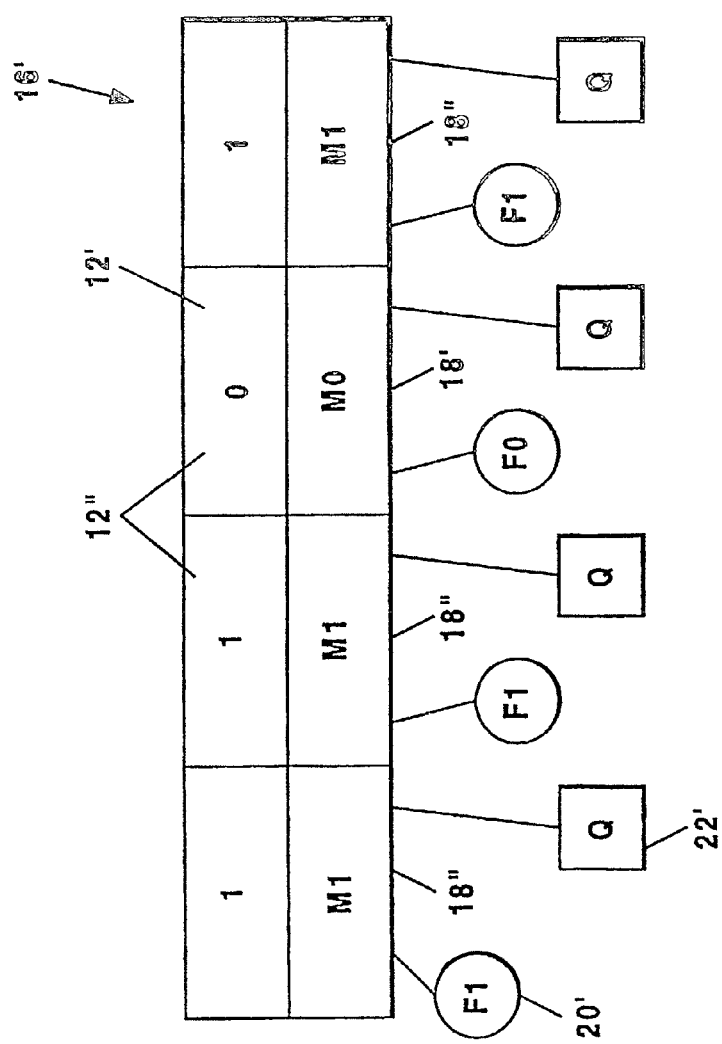
FIG. 4 is a schematic representation of a Beacon-Design Polymer complex.

FIG. 4 depicts the hybridization of a single-stranded Design Polymer 24 with molecular beacon "M1" 18" or "M0" 18' forming a BDP complex 24. In this BDP complex 24, M1 molecular beacons 18" hybridize to Design Monomers "1" 12", whereas M0 molecular beacons 18' hybridize with Design Monomers "0" 12'. As depicted in FIG. 4, M1 molecular beacons 18" have fluorophore "F1", whereas M0 molecular beacons 18' have fluorophore "F0". These two fluorophores emit a different wavelength signal, e.g., F1 could emit blue while F0 could emit orange.

Because the present methods involve conversion of a target polynucleotide into a binary code-based polymer, i.e., a Design Polymer, the present method requires only two fluorophores. One fluorophore represents "0" and the other fluorophore represents "1" of the binary code "0"+"1". Those skilled in the art will appreciate that other signal molecules can be employed consistent with what has been described herein.

The Beacon-Design Polymer complex can now be introduced to a nanopore system. The nanopore system of the present invention, for example, protein channels such as the bacterial alpha-Hemolysin (α-HL), can be used to obtain information on the length and sequence of polynucleotides and to detect the stochastic binding kinetics of different analytes to modified portions of the pore. See, Kasianowicz, J., et al., 1996, PNAS USA, 93, 13770-3; Akeson, M., et al., 1999, Biophys. J., 77, 3227-33; Meller, A., et al., 2001, PNAS USA, 97, 1079-1084; and Meller, A., et al., 2001, Phys. Rev. Lett., 86, 3435-38, the entire teachings of which are incorporated herein by reference. In one aspect, the polynucleotide is a single-stranded molecule such as a single-stranded Design Polymer. It is important to note that a plurality of nanopores can be used thus permitting the analysis of many Design Polymers, and, therefore, many target polynucleotides. In one aspect, the number of pores employed in a nanopore system ranges from 5 to about 10. It should be appreciated by those skilled in the art that many more pores can be employed.

A nanopore system can receive Design Polymers and analyze them based upon a given protocol. The nanopore system can comprise a variety of devices (including detectors) well known in the art. The nanopore system can be coupled to molecules, such as receptors, etc.

One skilled in the art will appreciate that chemical channels or pores can be formed in a lipid bilayer using chemicals (or peptides) such as Nystatin; ionophores such as A23187 (Calcimycin), ETH 5234, ETH 157 (all chemicals available from Fluka, Ronkonkoma, N.Y.; peptide channels such as Alamethicin, etc, employing methods well known in the art.

Nanopore systems that are within the scope of the present invention include those described in U.S. Pat. No. 5,795,782, U.S. Pat. No. 6,015,714, WO 01/81896 A1, and WO 01/81908 A1, the teachings of which are incorporated herein by reference.

The nanopore system of the present invention can have a pore molecule such as the receptor for bacteriophage lambda (LamB) or alpha-hemolysin. The apparatus used for the nanopore system comprises: (a) an ion-conducting pore or channel; (b) the reagents necessary for a Design Polymer to be characterized; and (c) a recording mechanism to detect changes in conductance of ions across the pore as the Design Polymer enters and proceeds through the pore. A variety of electronic devices are available which are sensitive enough to perform the measurements used in the invention, and computer acquisition rates and storage capabilities are adequate for the rapid pace of sequence data accumulation.

Other pore-forming proteins include Gramicidin (e.g., Gramicidin A, B, C, D, or S, from *Bacillus brevis*; available from Fluka, Ronkonkoma, N.Y.); Valinomycin (from *Streptomyces fulvissimus*; available from Fluka), OmpF, OmpC, or PhoE from *Escherichia coli, Shigella*, and other Enterobacteriaceae), Tsx, the F-pilus, and mitochondrial porin (VDAC).

Channels and pores useful in the invention can vary (e.g., minimum pore size around 2-9 nm). Pore sizes through which a polymer is drawn will be e.g., approximately 0.5-2.0 nm for single stranded DNA.

There can be multiple pores embedded in the same membrane. The combination of many pores (e.g., nanopores) embedded in the same membrane, or "nanopore array," the optical readout platform described in this invention lends itself for considerable parallelism in signal readout. Investigators have recently shown that using a state of the art Electron Multiplying CCD camera, they can achieve a readout of 256×256 pixels area at a frame rate of >200 frames per second. Importantly, it has been shown that one can resolve light emitted from individual fluorophores in this frame rate. This demonstrates that one can achieve a highly paralleled readout. In principle, an array of 100×100 pores fabricated in solid-state film can be imaged using a single CCD camera. Thus, a readout throughput can be boosted by ~4 orders of magnitudes as compared to a single nanopore throughput.

The human genome contains ~3×10$^9$ basepairs. A method that enables rapid and inexpensive genome sequencing must be highly paralleled. In one aspect, the readout speed of the present invention for 500 bases per second per nanopore will yield total readout of 5×10$^6$ nucleotides per second in a single chip containing 100×100 pores. This amounts to a single readout of the entire humane genome in ~10 minutes, an increase of 4-5 orders of magnitude over state of the art methods.

A modified voltage-gated channel can also be used in the invention (whether naturally or following modification to remove inactivation) and has physical parameters suitable for e.g., polymerase attachment (recombinant fusion proteins) or has a pore diameter suitable for polymer passage. Methods to alter inactivation characteristics of voltage gated channels are well known in the art (see, e.g., Patton, et al., Proc. Natl. Acad. Sci. USA, 89:10905-09 (1992); West, et al., Proc. Natl. Acad. Sci. USA, 89:10910-14 (1992); Auld, et al., Proc. Natl. Acad. Sci. USA, 87:323-27 (1990); Lopez, et al., Neuron, 7:327-36 (1991); Hoshi, et al., Neuron, 7:547-56 (1991); Hoshi, et al., Science, 250:533-38 (1990), the entire teachings of which are incorporated herein by reference).

In one aspect of the present method, the nanopore is α-HL. See, U.S. Pat. No. 6,528,258, the entire teaching of which is incorporated herein by reference.

The α-HL pore consists of two main parts: a ~2.5 nm diameter cavity ("vestibule") and a ~1.5 nm diameter channel ("stem"), which permeates the cell membrane. Double stranded polynucleotide domains can be lodged in the 2.5 nm vestibule part but they cannot enter the 1.5 nm channel (the diameter of dsDNA is roughly 2.2 nm). Recently it has been demonstrated that the closing-opening kinetics of short blunt-ended DNA hairpins (from 3 to 8 base pairs) can be directly measured using the nanopore, by lodging the hairpins in the α-HL vestibule, and detecting the time required for their thermally-activated opening. Upon the spontaneous opening of the hairpin, the single strand DNA enters the 1.5 nm channel, causing a brief (but discernable) blockade in the ion current flowing through the pore, thus permitting the detection of the time interval from hairpin (or double-stranded polynucleotide) lodging to its first opening.

Figure 5:
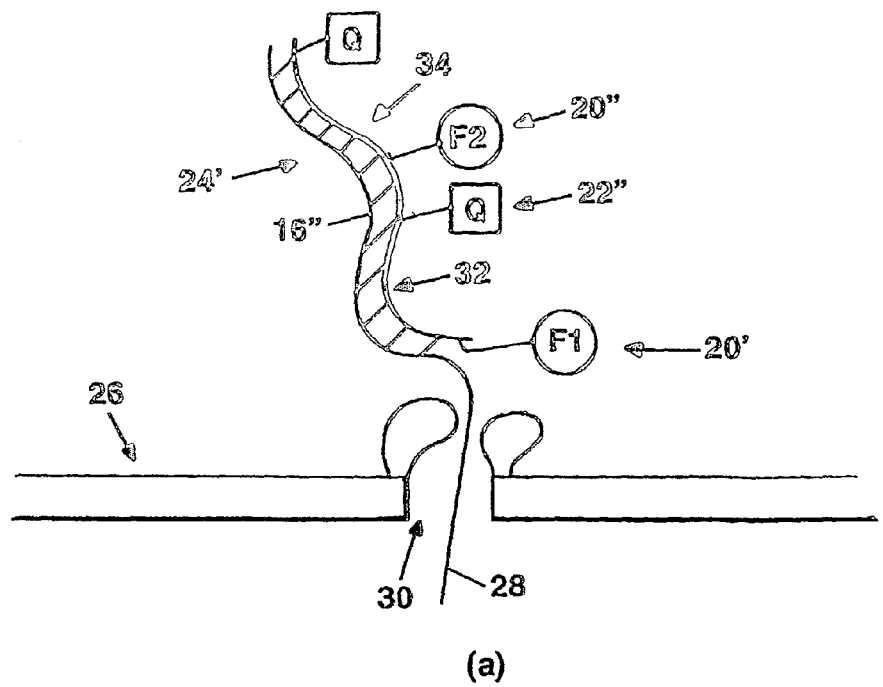
FIG. 5 is a schematic representation of the translocation process of the Beacon-Design Polymer with the nanopore where (a) shows the initial steps involved in this translocation process, and (b) illustrates a later stage of the process.
Figure 5:
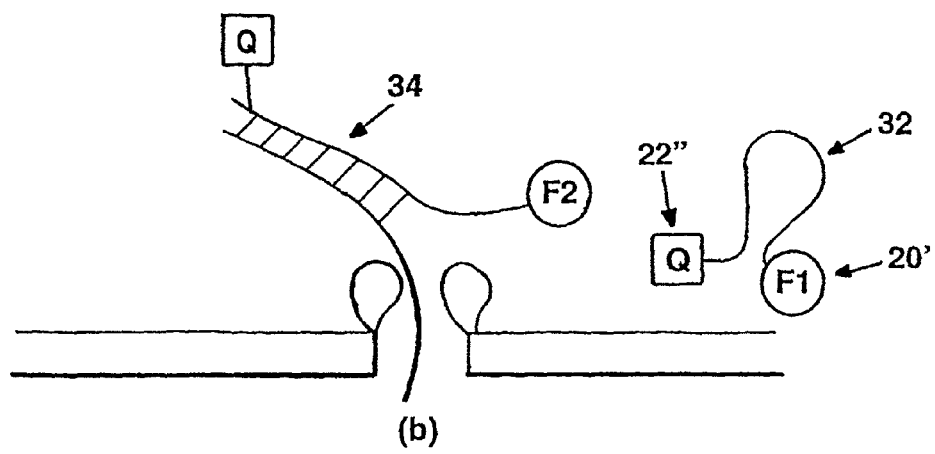

Referring to FIG. 5, a Beacon-Design Polymer complex 24' is introduced to the nanopore system 26. As depicted, a single strand 28 of the Design Polymer 16" is threaded through a pore 30 of the nanopore system 26. In one aspect, the single strand portion is the 3' end of the Design Polymer 16". The driving force for movement of the single strand 28 Design Polymer 16" is provided by an electric field that is established across the nanopore 26. Through the use of two electrodes, an electric field is applied and is used to "unzip" the double-stranded Beacon-Design Polymer complex 24'. This field also provides the driving force for entry of a resulting single-stranded Design Polymer 16" into the nanopore. As the unzipping occurs, the molecular beacon moieties 32, 34 are relieved from their interaction with the Design Polymer 16" at or near a channel 30 of the system 26 itself. As the first leading beacon is removed from the BDP complex 24', the subsequent fluorophore becomes liberated from the quencher of the first beacon, thus the fluorophore can light up and be detected by an appropriate detector. For example, molecular beacon 32 in FIG. 5 has a quencher 22", which quenches the signal of fluorophore F2 20" that is located on molecular beacon 34. When the first molecular beacon 32 is unzipped and removed from the B-D complex, fluorophore F2 20" will be freed from the influence of quencher 22", thus it will elaborate its signal. See, FIG. 5b. The first molecular beacon 32 will self-hybridize and consequently its quencher 22" moiety will quench its fluorophore F1 20'. This self-quenching mechanism minimizes the background noise. This process can be repeated until the entire Design Polymer 16" has been analyzed.

In summary, the foremost fluorophore of the hybridized (to the Design Polymer) molecular beacon is detected and registered at the same time when a voltage ramp is applied in order to unzip (or melt off) the hybridized beacon from the Design Polymer. As discussed above, unzipping occurs roughly 10 ms after the beginning of the voltage ramp, providing sufficient time for the registration of the fluorophore. The unzipping results in the release of the first beacon and the immediate exposure (un-quenching) of the next fluorophore hybridized to the Design Polymer. The released beacon will immediately self-hybridize, self quenching its own fluorophore. The change in the fluorescence intensities (of either of the two colors) is detected and triggers the application of the next voltage ramp. The cycle repeats until the entire Design Polymer is read. In one aspect, the Design Polymer has a hairpin. The final hairpin is disposed at the 5' end of the Design Polymer to force the molecule to enter the nanopore system in one direction only, i.e., the single-stranded 3' end. Upon completion of the translocation of the Design Polymer into and through the nanopore system, an optical system (discussed below) will sense that the polymer readout has finished (that the DNA cleared the pore) when the ion current will rise to the open pore level.

Force-induced unzipping of longer double-stranded helical domains (50 bp) of DNA has been demonstrated using the α-HL pore. See, Sauer-Budge, A. F., et al., 2003, Phys. Rev. Lett., 90, 238101, the entire teaching of which is incorporated herein by reference. It was found that the characteristic passage time of the molecules, which includes the sliding of the single strand through the pore, plus their unzipping time, follows an exponential dependence on the applied voltage (in the range 140-180 mV). Thus the voltage applied to unzip the beacons in the current invention can be used as a sensitive control parameter to determine the time delay between each unzipping step (of successive beacons along the DNA). This was shown in detail in our recent data (FIGS. 10-15).

Voltage controlled unzipping is described in Biophysical Journal: Mathé J. et al. 2004 Biophys. J. 87, 3205-12, the entire teaching of which is incorporated herein by reference. This paper demonstrates that short oligonucleotides (~10 bases) hybridized to a long complementary single stranded DNA can be unzipped inside a nanopore in a voltage-controlled manner, and that the characteristic time scale of the unzipping process strongly depends on the voltage, further, it can be selected to be in the range of 1-10 ms. This time scale is highly important, it demonstrates that: (a) the translocation speed of DNA in a pore can be regulated and, in particular, it can be slowed down by the unzipping of DNA probes. The amount by which the translocation is slowed down depends exponentially on the interaction strength between the DNA and the hybridized probed, as well as on the applied voltage. Thus, by selecting the sequence of probe, different levels of "slowing down" can be achieved. It was also shown that the applied voltage can be used to adjust the unzipping and, thus, translocation speed. Slowing down of the DNA translocation has been a long-standing problem in this field; and (b) investigators were able to slow down the translocation to speeds range that is compatible with single fluorophore optical detection (0.1-50 ms per base). Without this slowing down, photon noise will dominate the readout wherein a single fluorophore readout cannot be realized using existing technology.

Optical agents for use in accordance with the present invention comprise, for example, fluorescent molecules that are quenched when brought into close proximity with a quencher molecule. Extensive literature is available describing fluorescence and the other types of compounds that exhibit this behavior, as well as the particular properties (e.g., fluorescence decay time, absorbance spectra, emission spectra, photostability, and quantum efficiency) of these compounds (see, for example, Gilbert et al., Essentials of Molecular Photochemistry, CRC Press, 1991; Laxowicz, J R, Principles of Fluorescence Spectroscopy ($2^{nd}$ ed.), Kluwer academic 1999; the entire teaching of which is incorporated herein by reference). Detailed descriptions of fluorescence quenching are available, for example, Kavarnos et al., Chem. Rev. 86:401, 1986; Wagoner, Methods Enzymol. 246:362, 1995; Millar, Curr. Opin. Struct. Biol. 6:637, 1996; Petit et al., Biol. Cell 78:1, 1993; the entire teachings of which are incorporated herein by reference.

In recent years, there has been much progress made in the detection of single fluorescent molecules (see, e.g., Mathis et al., Bioimaging 5:116-128, 1997; Ha et al., Proc. Natl. Acad. Sci. USA 93:6264-6268, June 1996; Goodwin et al., Acc. Chem. Res. 29:607, 1996; Muller et al., Chem. Phys. Lett. 262:716, 1996; Sauer et al., Chem. Phys. Lett. 254:223, 1996; the entire teachings of which is incorporated herein by reference). Such molecules possess characteristic fluorescence decay times that are sensitive to the molecule's electronic environment and therefore can be quenched by association with polymers that alter the environment.

Examples of fluorophores that can be used with the present invention include TMR and Cy5. Other types of fluorescent molecules that can be used are CPM, the Alexa series of fluorescence markers from Molecular Probes, Inc., the Rhodamine family, and Texas Red. Other signal molecules known to those skilled in the art are within the scope of this invention. Numerous other fluorophores can be used in the present invention including those listed in U.S. Pat. No. 6,528,258, the entire teaching of which is incorporated herein by reference.

Quenching molecules that can be used in the present invention include Dabcyl, Dabsyl, methyl red and Elle Quencher™. Other quencher molecules known to those skilled in the art are within the scope of this invention.

The detection system employed in the present invention depends upon the optical agents being used. The detection system must be capable of detecting changes in optical properties of an optical agent on the time scale relevant to the sequencing method described herein. In one aspect, fluorophores are employed as optical agents. A suitable fluorescence detector therefore would be appropriate. Those skilled in the art are familiar with fluorescence detectors.

Figure 6:
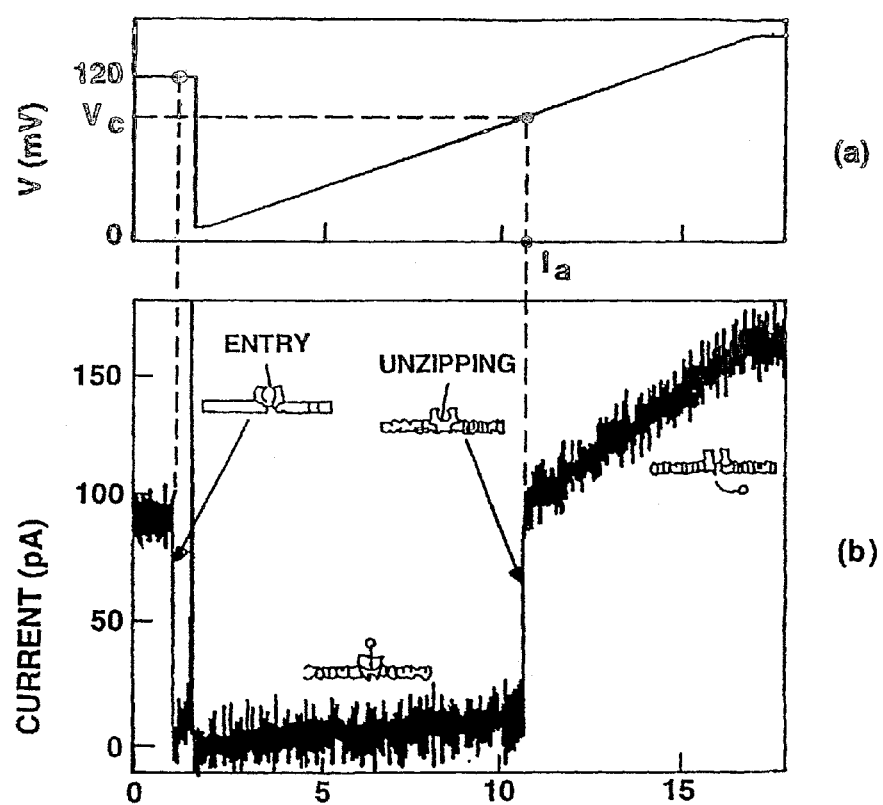
FIG. 6 is a graph showing the results from unzipping a 10 bp hairpin DNA using active control, where (a) displays the applied voltage vs time (in milliseconds), and (b) displays the measured ion current through the pore.

Referring to FIG. 6, panel (a) displays the applied voltage versus time (in milliseconds). The voltage ramp of the nanopore system is triggered in real-time analysis of the ion current flowing through a single nanopore channel as the single-stranded polynucleotide enters the pore. In approximately 0.1 ms after the entry of the single-stranded polynucleotide into the nanopore (as signaled by an abrupt drop in pore current), the voltage is reduced to a "holding" level and then it increases at a constant rate. FIG. 6b displays the measured ion current through the pore. After the entry of the single-stranded part of the molecule into the channel, the pore current is reduced to its blocked level (~10% of the open pore current or ~10 pA). When the voltage ramp begins, the current initially stays at its blocked level, but at t~10 ms the current abruptly rises to the open pore level because the double-stranded polynucleotide unzips and rapidly clears the pore (clearing of the pore lasts less than 0.05 ms). The unzipping voltage (dashed line) can be readily measured.

Figure 7:
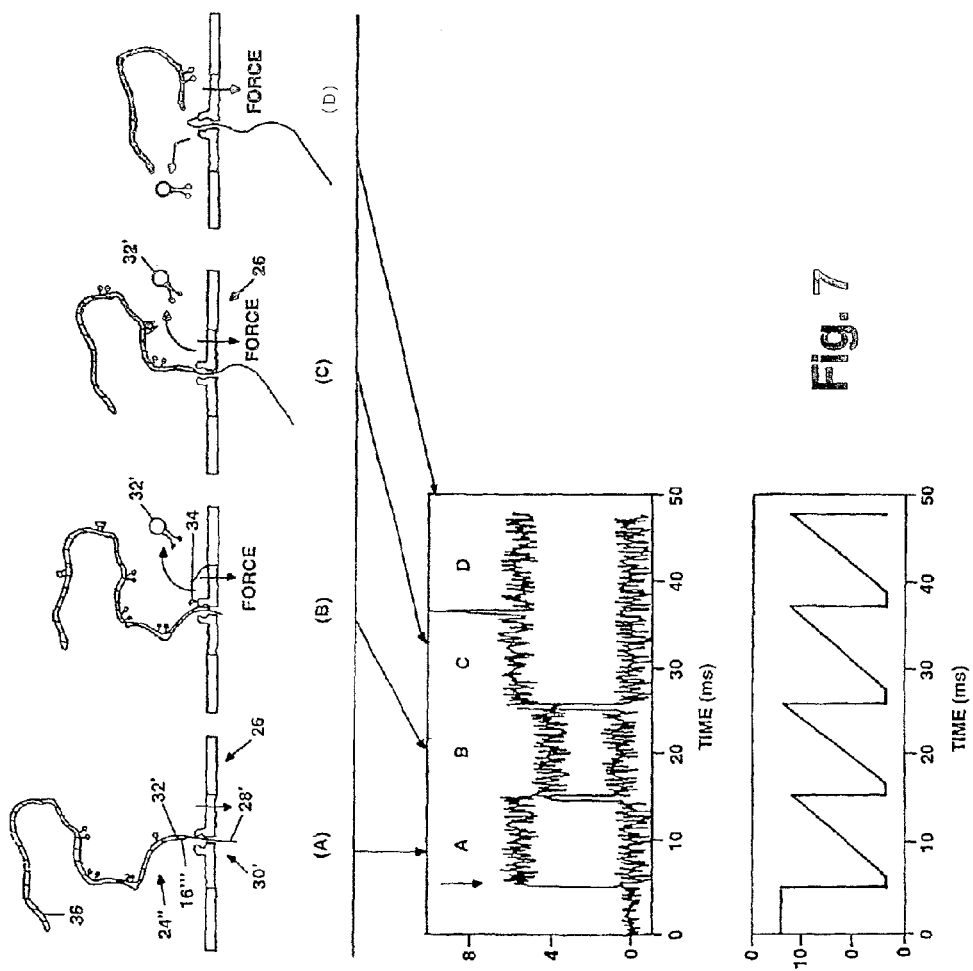
FIG. 7 depicts four distinct steps indicated by (A), (B), (C), and (D) are displayed that occur in a typical analysis of a sample polynucleotide where the upper panel displays schematic drawings of the translocation of a Design Polymer into and through a nanopore system, the middle panel depicts the photon counts/ms vs. time, and the bottom panel depicts the voltage being registered.

Referring to FIG. 7, four distinct steps indicated by (A), (B), (C), and (D) are displayed that occur in a typical analysis of a sample polynucleotide. These steps can be repeated until the sequencing is completed. The top panel depicts the entry and transition of a BDP complex 24'' through a nanopore channel 30. The middle panel depicts the photon counts/ms vs. time, and the bottom panel depicts the voltage being registered.

At step (A), the readout begins when the single-stranded overhang of the Design Polymer 28' enters pore 30' as it is pulled in by an electric field. The abrupt reduction in the ion current flowing through the pore 30' due to the entry of the Design Polymer 28' triggers the readout by: 1) reducing the voltage from the "driving" level down to the "hold" level and the initiation of the first voltage ramp; and 2) switching on, for example, a laser for fluorescence analysis. Because, the first beacon hybridized to the Design Polymer is not quenched, an immediate increase of its corresponding fluorescence level will be produced, (shown as a light trace in the middle panel). Note that the typical unzipping time is ~10 ms. In that time photons emitted from the first unquenched fluorophore will be registered by an appropriate detector.

Step (B) is initiated immediately after the first beacon 32' is unzipped. The unzipping of the molecular beacon 32' will permit the single-stranded Design Polymer 16' to move further inside the nanopore 26. This unzipping process results in the un-quenching of subsequent fluorophores by releasing molecular beacons. The released beacons will automatically self-hybridized due to thermodynamic forces, thus, a beacon's own fluorophore will be quenched. The self-hybridized beacons will eventually diffuse away. Advantageously, this feature will help to avoid or minimize background noise. The resulting fluorescence signal (middle panel) shows an increase in the red (dark) emission corresponding to fluorophore 34, and a decrease in the orange (light) emission corresponding to the loss of and self-hybridization of molecular beacon 32'. There is a small (about 50 μs) delay in the quenching of the first beacon 32' due to the finite time that it takes for the beacon to self quench. During this small delay time there are fluorescence intensities from both fluorophores 32' and 34 which can be used to pinpoint the transitions, used to trigger the voltage ramps.

In step (C), there is a similar readout to the first beacon 32', shown by the lighter line. Note that between steps (C) and (D), where both beacons from the same type are read, there is a spike in the orange intensity (light gray). This is due to the contribution of two fluorophores as explained above. In this way the system reads the entire Design Polymer. To prevent the entry of the Design Polymer 16''' into the pore from its 5' (rather the 3'), a 7 bases hairpin 36 can be added during the Design Polymer's 16''' conversion process. This hairpin 26 is eventually unzipped allowing for complete translocation of the Design Polymer 16''' into the inside or vestibule of the nanopore system 26.

The present invention also pertains to an apparatus for determining the sequence of a polynucleotide. An optical system 300 for the detection of fluorescence signals from individual DNA molecules, threaded inside a membrane embedded nanopore is described herein.

Figure 8:
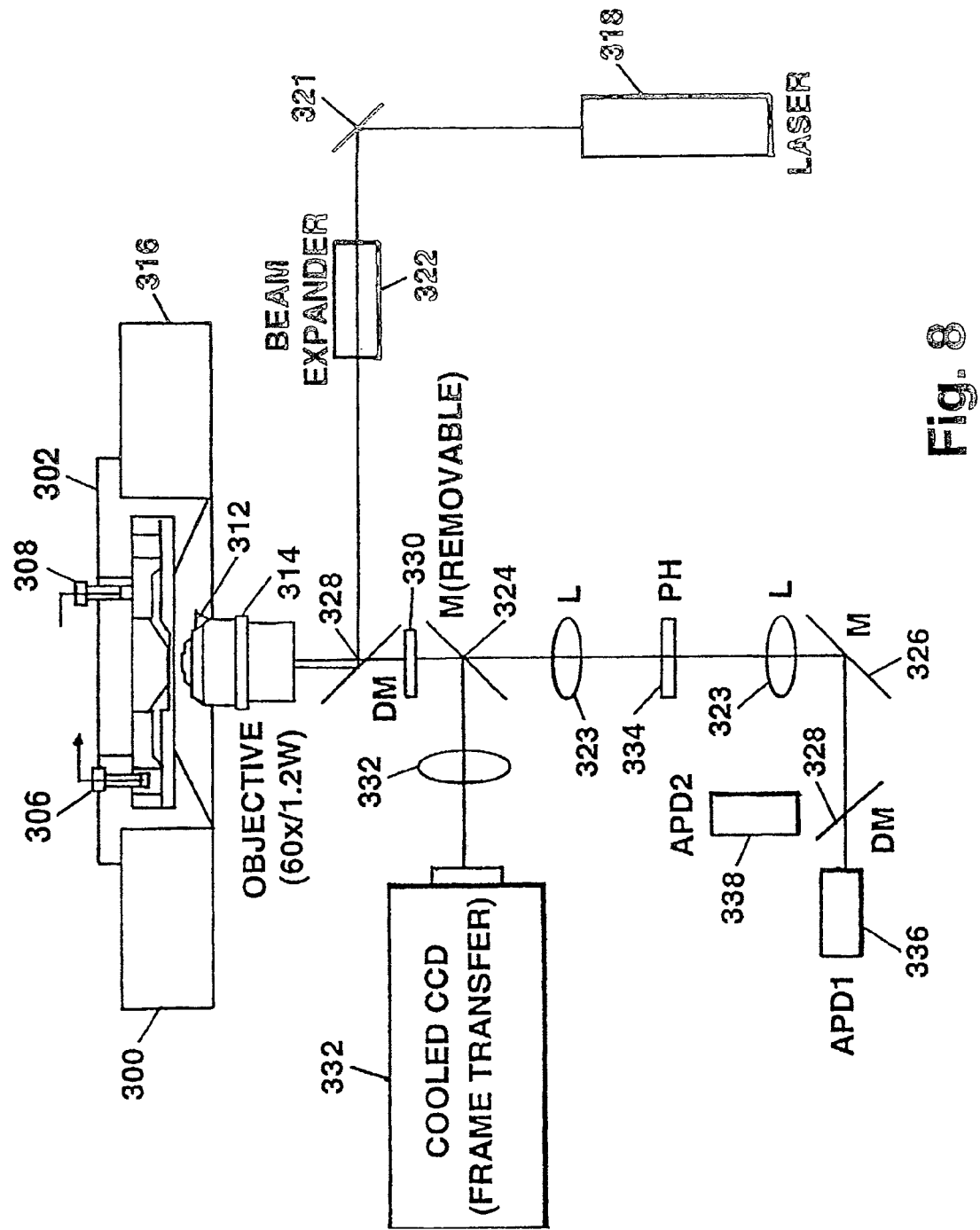
FIG. 8 is a schematic drawing of an optical system used in conjunction with a nanopore system.

FIG. 8 is a schematic of optical system 300 that can be used in conjunction with the sequencing method of the present invention where the system 300 comprises elements required for detection of optical signals. Specifically, FIG. 8 illustrates an optical setup for the optical detection of single-molecules using one or more bilayer membranes.

The present optical system 300 comprises a custom made flow cell 302 comprising a nanopore support 304 and two electrodes 306 and 308. Electrodes 306 and 308 are used to apply an electric field required for the unzipping process while support 304 enables the suspension of a phospholipid bilayer 310 in the proximity of a glass coverslip 312 thereby enabling imaging of the bilayer 310 using a high-power microscope objective 314. Flow cell 302 is mounted in an XYZ nanopositioner 316 in a custom made inverted microscope and can be mobilized for precision alignment with the optical axis 208 using a translation stage.

Fluorophores can be excited by an emitted light from a diode laser 318 into the optical system 300. The laser 318 can be a 532 nm solid-state laser (e.g., New Focus™ 3951-20 or Point Source iFLEX 2000™) and coupled with a single-mode, polarization preserving, optical fiber 320. The laser beam is steered via a mirror 321 expanded using an home made adjustable beam expander (5×) 322, and directed to a back aperture of objective 314 using mirrors 324 and 326 and a dichroic mirror 328 (Chroma z532 rdc).

The laser beam is slightly expanded at the focal point of objective 314, to allow a larger illumination area. The expansion of the beam is accomplished by slightly diverging the incoming expanded laser beam at the entrance to microscope objective 314. By moving one of the lenses on the beam expander 322 with respect to the other one, the beam is slightly defocused at the focal point of objective 314 and achieves a larger illumination area (~10 µm). The fluorescence emission is collected using the same objective 314 and filtered using a long pass filter 330 (Chroma hq560 lp). Light is then imaged either by a frame transfer back illuminated cooled CCD camera 332 or by first focusing the light onto a pinhole 334 and imaging the pinhole onto two avalanche photodiode point detectors 336 and 338 (Perkin Elmer SPCM AQR-14) for fast detection. The optical system 300 (excluding the excitation and emission paths) is wholly enclosed in a shielded copper box (not shown) to reduce electromagnetic noise pick up. By using CCD camera 332, several pores will be allowed to be imaged simultaneously, thus multiplying the throughput of detection system 300.

Instrument control and data acquisition software is used to control automatic positioning and imaging of single molecules and for the real-time nanopore force spectroscopy. The master trigger for both the fluorescence and current data acquisition is the blocked current signal of a single molecule entering nanopore 302. The hardware electronics comprise three PC boards: a fast digital I/O to interface with the PZT controller (Physik Instrumente PI-E710), a photon counter board (National Instruments PCI-6602), and a fast A/D board that samples the ion current and produces a programmable voltage gradient across the pore (e.g., National Instruments PCI-6052E).

Figure 9:
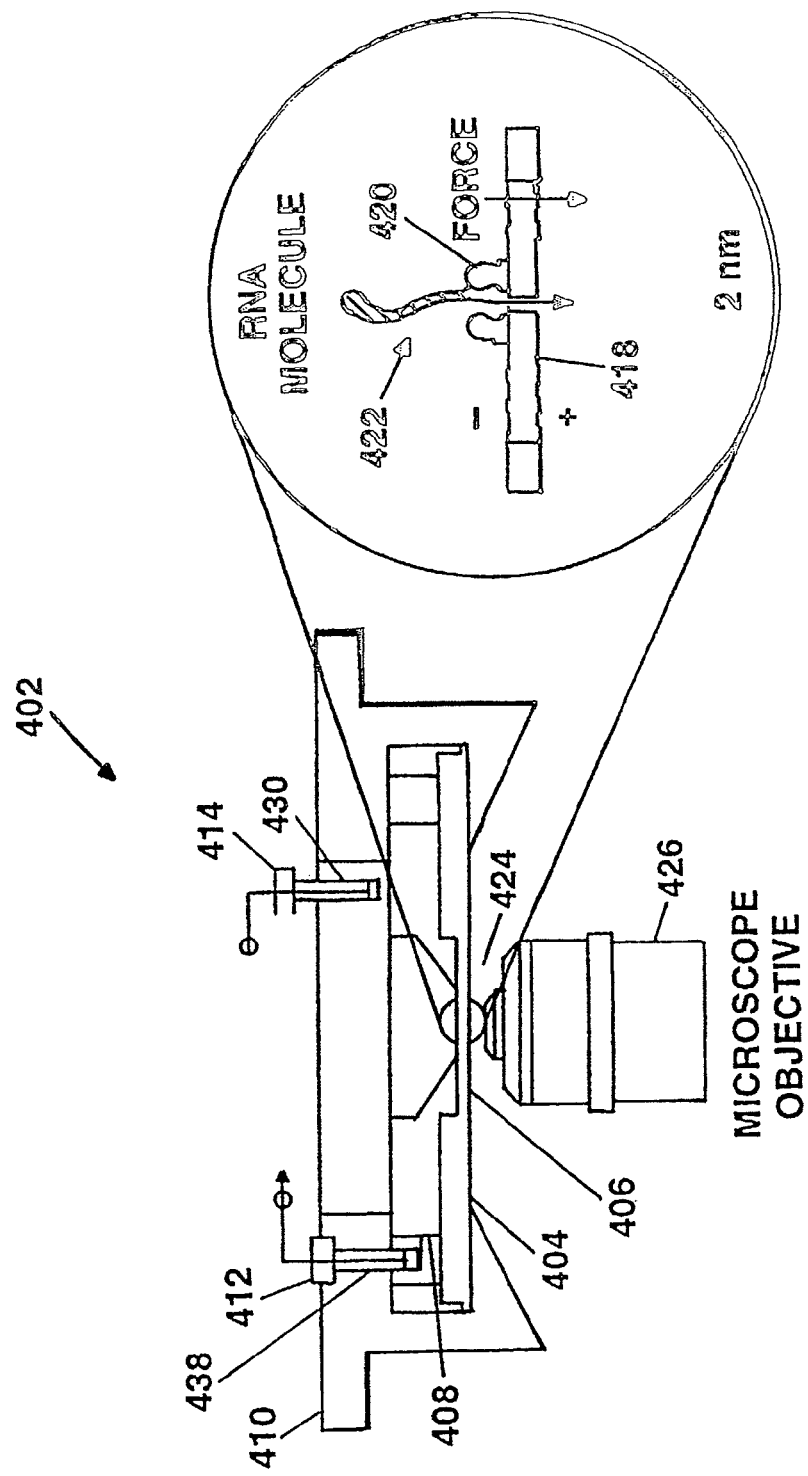
FIG. 9 is an enlarged portion of the optical system depicted in FIG. 8.

The instrument is comprised of custom made microfluidic cells used to support an approximately 20 µm phospholipid bilayer horizontally, and to exchange buffer solutions. Referring to FIG. 9, a micro-fluidic cell 402 is depicted comprising (a) quartz substrate 404, (b) custom machined Polytetrafluoroethylene (PTFE) film 406, (c) chamber made of poly-dimethylsiloxane (PDMS) 408, (d) housing 410, and (e) electrodes 412 and 414. A 20-30 µm aperture 416 is fabricated in PTFE film 406 by mechanical imprint. Inset 416 illustrates membrane 418 and the α-HL pore 420 containing an RNA molecule 422 where membrane 418 is supported by aperture 416.

Figure 10:
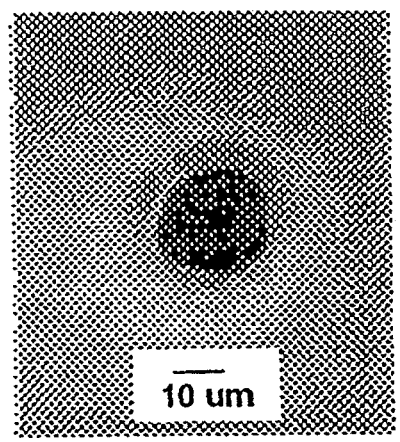
FIG. 10 is an SEM image of a ~30 μm hole fabricated in a thin Teflon® (polytetrafluoroethylene, PTFE) film.

FIG. 10 shows an SEM image of ~30 µm aperture 416 fabricated in PTFE film 406. Membrane 418 is suspended in circular aperture 416 within 12 µm thick PTFE film 406, approximately 100 µm above the glass coverslip 424. This enables high-resolution fluorescence imaging of membrane 418, using a 60×/1.2 N.A. water immersion microscope objective 426 (Olympus UPLAPO60XW). This is in contrast to prior art designs where oil immersion is used. The use of water immersion objective 426 (high NA) rather than an oil immersion objective, provides a longer working distance (~250 µm). PTFE film 406 separates two small chambers 428 and 430 (about 50 µl each) that can be accessed for fluid exchange by special tubing. Two Ag/Ag—Cl electrodes 412 and 414 are in contact with the fluid chambers 428 and 430 and are connected to a high resolution patch clamp head-stage amplifier (not shown) (e.g. Axon Instruments 200 U) used to apply voltage across the membrane.

Returning to FIG. 9, a nanopore, for example, a α-HL pore 420 is embedded in membrane 418 using a method described in the literature (see, e.g., Meller, A., et al. (2000) Proc. Natl. Acad. Sci. U.S.A. 97, 1079-1084; Meller, A., et al. (2001) Phys. Rev. Lett. 86, 3435-3438, all incorporated by reference), and the ionic current flowing through pore 420 is measured using the patch-clamp amplifier and analyzed in real-time. As discussed above, cell 402 is mounted on an XYZ nanopositioner (e.g., Polytec PI-P527.3CL) to allow precise alignment of cell 402 and nanopore 420 at the field of view of the objective, and to track fluorescently labeled nanopore 420 laterally based on real-time analysis of the signal.

There are at least two different embodiments of the membrane cell that are within the scope of this invention. A membrane cell can be made by embedding PTFE film in a custom made PDMS gasket that has an upper fluid chamber and lower fluid chamber. PDMS gasket is housed in a supporting plastic cap. The cell is about 25 mm wide and about 3 mm thick. It includes a lower chamber (~10 µl) that can be accessed using tubing. The Ag/AgCl electrode of the lower chamber and PTFE film are embedded in the PDMS gasket. The cell is covered from the bottom face with glass coverslip through which imaging is made.

Alternatively, the membrane cell can be composed of two concentric cylinders, an upper chamber and a lower chamber that can slide with respect to each other by fine micrometers. At the bottom face of upper chamber, PTFE film is fused by heat. The upper chamber is free to slide down inside lower chamber until the PTFE film approaches the coverslip and can be imaged from below with the microscope. Approximately 20 µm circular aperture can be fabricated in using a PTFE film which is used to support a lipid bilayer. The lower chamber is a ~20 mm wide chamber (6 mm high) and supports a thin glass cover slip disposed at its bottom face. The cell is connected to fluid tubing and two electrodes.

One embodiment of the present invention is directed to quantifying the number or amount of a polymer in a given sample matrix. For example, the polymer can be a polynucleotide. In one aspect, a pre-determined polymer is putatively in the sample. In this aspect at least some portion of the sequence is known. This portion can range from about five to about fifty or greater nucleotides. Using methods of the present invention, Design Monomers can be designed to hybridize to the polynucleotide of interest and employing the nanopore system described herein, the target polynucleotide can be detected and measured.

Another embodiment of the present invention is directed toward the detection of a polynucleotide in a sample matrix. Design Monomers specific for a pre-determined nucleotide sequence can be constructed. These Design Monomers can be introduced to the sample containing polynucleotides. The sample can be a heterogenous or homogenous sample. The Design Monomers are introduced to the sample under conditions suitable for hybridization which are well known to those skilled in the art. Using the methods of the present invention, those polynucleotides that hybridized to the pre-determined design Monomers can then be isolated and/or processed.

The detection of specific polynucleotide sequences can be effectuated by the methods of the present invention. For example, the fidelity of the polymerase used in PCR is not 100% and therefore polynucleotides produced using PCR have to be monitored for their fidelity of sequence. Using the methods described herein, a practitioner can verify the fidelity of the polymerase and the overall PCR process. Pre-determined Design Monomers can be constructed, reflecting a portion of a target polynucleotide, forming a Design Polymer that can be subsequently sequenced using the present methods.

One embodiment is directed toward the detection of a single or a plurality of mutations in a given polynucleotide sequence. Assuming that the target sequence is known in part or in its entirety, Design Monomers can be constructed such that the examination of a polynucleotide sequence can be accomplished. The Design Monomers can be introduced to a sample matrix having a putative target polynucleotide under conditions suitable for hybridization forming a Design Polymer. This construct can then be subjected to the methods of the present invention for sequencing. A mutation will be reflected by one or more Design Monomer mismatches.

One embodiment of the present invention is directed towards information storage. Given that the present invention utilizes a binary code for any polynucleotide sequence, a nucleotide sequence can be stored using only the binary code. In one aspect, a Design Polymer can be designed to code a sequence of numbers ("0" and "1") just like a computer file. In a sense, DNA can be considered a static, ultra dense, storage media. The nanopore system of the present invention is an efficient means to retrieve (read) the information coded in the sequence.

It should be understood by one skilled in the art that the methods described herein have numerous practical applications that do not depart from the scope of the present invention.

EXAMPLE

Nanopore Unzipping of Individual DNA Hairpin Molecules Using α-HL

In order to enable nanopore measurements with time-dependent electric fields such as with a sequencing method, an unzipping method has been developed. The present unzipping method uses high voltage to optimize the entry rate into a pore, while the unzipping voltage is kept variable. Thus, hundreds of individual molecules can be probed over a short period of time (few minutes). The method allows a practitioner to rapidly change the electric field applied across the nanopore during the passage of a polynucleotide.

This unzipping method is particularly advantageous in studying the unzipping kinetics of individual DNA hairpin molecules, over a wide range of voltages from 30 mV to 150 mV and at different loading rates (0.5 V/s-100 V/s). Moreover, the method allows dynamic force measurements in which a constant loading rate is applied rather than a constant force. These two complementary measurements allow small enthalpy changes in the DNA hairpin to be resolved down to 1 kcal/mol.

There are three consecutive steps in the nanopore unzipping process of the DNA hairpins: (A) the entry and sliding of the single-strand DNA overhang (50 nt), until the double-stranded (helical) part itself is lodged in the 2.5 nm vestibule of the α-HL; (B) the unzipping of the helical part; and (C) translocation of the unzipped single strand part through the pore.

Referring to FIGS. 11-17, the steps were characterized, in order to resolve their typical time scales at different voltages. By using the active voltage control method, the overhang entry (part A) can be decoupled from the other steps, and that the translocation time of the unzipped strands (part C) is much shorter than the typical unzipping time and thus can be neglected.

Firstly, the experiments characterized the time scale associated with single-stranded DNA ("ssDNA") threading in a pore as a function of voltage by showing that the typical time scale for unzipping a 10 bp hairpin is substantially longer than the threading time of the ssDNA. Next, the unzipping kinetics information for stationary (or step function) voltages in the range 30-150 mV was displayed to determine the effective charge on the DNA strand inside the pore. Finally, the experiment demonstrated the dependence of the unzipping kinetics on the loading rate. The data was interpreted using a simple theoretical model similar to the one developed for other single molecule ("SM") unbinding experiments.

Materials and Methods

PAGE-purified ssDNA and DNA hairpins (Eurogentec, San Diego, Calif.) were buffered in a 10 mM Tris, 1 mM EDTA, pH 8.5 solution and, prior to the measurements, were heated to 75° C. for 10 minutes and then quenched to 4° C. The hairpin molecules consisted of a 3' single stranded overhang (50 mer poly-dA (SEQ ID NO: 19)), and a 10 bp helical part containing an intervening 6 base loop with the following sequence (the self-complementary parts are underlined):

```
                                              (SEQ ID NO. 1)
HP1:     5'-GCTCTGTTGCTCTCTCGCAACAGAGC(A)₅₀;
```

In addition, a similar hairpin (HP2) with a single (TT) mismatch on the 5th base from the 5' end, was also prepared with the following sequence:

```
                                              (SEQ ID NO. 2)
HP2:     5'-GCTCTGTTGCTCTCTCGCAACTGAGC(A)₅₀;
``` and also a 7 bp helix hairpin (HP3), with the following sequence:

```
HP3:    5'-GTCGAACTTTTGTTCGAC(A)₅₀;    (SEQ ID NO. 3)
```

(The basic apparatus and experimental method used for reconstituting the α-HL channel in a horizontally supported planar lipid bilayer is described above.) The temperature of the system was maintained at 15.0±0.1° C., using a custom cell design. The buffer solution was 1M KCl, 10 mM Tris-Hcl, with a pH of 8.5. The α-HL open pore conductance under these conditions was 0.82 pS in the forward bias. The ion current was measured using a patch-clamp amplifier (Axopatch 200B, Axon Instruments, Union City, Calif.) and the signal was filtered using a 100 kHz low-pass 4-poles Butterworth filter (Krohn Hite 3302, Avon, Mass.). The signal was digitized at 1 MHz/22 bits using a DAQ card. All control and acquisition software was written using National Instruments' LabView. The apparatus incorporates a feedback loop used to control the applied transmembrane voltage. The response time of the membrane potential to a step in the control voltage was 4±1 μs. In each experiment (performed at given conditions set by the voltage or the voltage ramp) data was typically collected over 1,000 unzipping events. The software and hardware combination permits high-throughput unattended data acquisition, such that the total acquisition time for each experiment was ~10 minutes.

Each unzipping event consisted of three parts: 1) Threading and sliding the single stranded overhang until the helical part was lodged inside the vestibule of the α-HL; 2) Holding the hairpin inside the pore at low voltage; and 3) Unzipping the double-stranded DNA.

The first and the second parts were designed to prepare the system for the third part, such that unzipping always starts at a given configuration of the molecule with respect to the pore.

As with any single molecule experiment, variations between molecules or events are unavoidable. There were a set of control measurements (described below) and the unzipping experiments were repeated many times in order to reduce data scatter. The unzipping part consisted of two types of measurements: unzipping at stationary force, and unzipping with a fixed loading rate. These experiments are described in the "Results" section.

Figure 11:
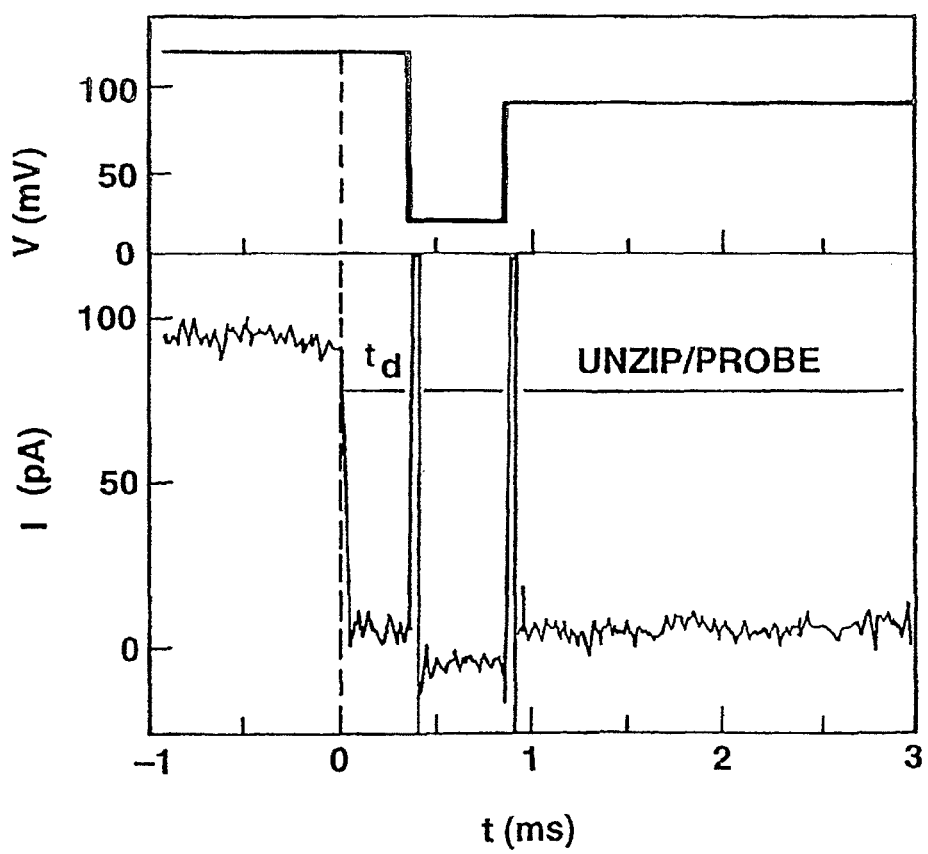
FIG. 11 is a graph showing the first few milliseconds (ms) of a typical unzipping event performed at a constant force. Where the upper panel shows a controlled voltage applied across the pore while the lower panel shows the pore current resulting from the applied voltage. At t=0 the DNA enters inside the pore.

The voltages and times selected for the first two parts (sliding and holding) were unchanged in all experiments. FIG. 11 shows the first few milliseconds (ms) of a typical unzipping event performed at a constant force. The upper panel displays the applied voltage as a function of time and the lower panel is the resulting pore current. The event begins with the threading of the single stranded poly(dA) end inside the pore. The entry of the polynucleotide into the channel is detected by the abrupt decrease in the open pore current, which sets off a trigger in the acquisition system and defines the t=0 point (dashed line). The molecule is drawn inside the channel at V=220 mV for a time $t_d$=300 μs. This time was chosen to be slightly larger than the most probable translocation time, $t_P$, of 40 mer DNA, as shown in the results. Therefore, at t=$t_d$ most of the DNA hairpins are expected to be fully lodged in the α-HL vestibule. This hypothesis was verified by two independent supplementary measurements: in the first experiment $t_d$ was varied from 50 to 700 μs and measured the distribution of escape times upon the reversal of the voltage to V=−120 mV at t=$t_d$. There was a monotonic increase in the typical time required for the molecules to be pulled away from the pore for $t_d$ values between 50 and 300 μs. But, for $t_d$>300 μs the curve saturated to a constant level, indicating that the single strand overhang of DNA was threaded through the channel and then stopped when the double-stranded helical part entered the vestibule. Further evidence came from the analysis of the level of the blocked ion current during $t_d$. Specifically, the average current (for $t_d$=300 μs) displayed two clear peaks: a major low-current peak at ~6 pA and a secondary peak at the normal poly(dA) blocked level (~11 pA). The lower current peak was attributed to additional blocking of the pore by the helical part of the hairpin occupying the α-HL vestibule.

The fraction of unzipped hairpins at t=$t_d$=300 μs was very small. This fraction was quantified by measuring the translocation probability distribution of the hairpin molecule at V=120 mV (data not shown). From this distribution it was estimated that the fraction of unzipped hairpins at t=$t_d$=300 μs was smaller than 0.5%. Following the initial sliding of the DNA, at t=$t_d$ the voltage was reduced to a low "holding" potential (20 mV) for a time $t_H$=500 μs. This voltage was found to be sufficiently large to keep the hairpins in the vestibule, but was too small to induce significant unzipping as evident from the data displayed below. The choice of 500 μs was dictated by convenience (in a separate set of experiments hairpins were held in the pore for up to 5 seconds). At the end of the holding period the unzipping voltage, $V_U$ (or the loading rate) $\dot{V}$=dV/dt was applied.

Results

The translocation time distributions of ssDNA.

The translocation time ($t_T$) of each individual DNA is defined as the time interval from the entry of the first few bases of the DNA molecule inside the channel part of the α-HL pore, to the exit of the molecule from the other side of the channel. These events are clearly observed by the abrupt reduction of the ionic current flowing through the pore down to ~10% of the open pore current. In the case of the hairpins, the DNA can only enter the channel with its single strand 3' overhang, since the loop at its other end is too large to enter the pore. In this case, $t_T$, is a sum of the three consecutive processes described above, i.e. $t_T$=$t_{s1}$+$t_{unzip}$+$t_{s2}$, where $t_{s1}$ is the sliding time of the single strand overhang (poly(dA)$_{50}$ (SEQ ID NO: 19)), $t_{s2}$ is the sliding time of the unzipped hairpin+loop (26 bases), and $t_{unzip}$ is the unzipping time.

Figure 12:
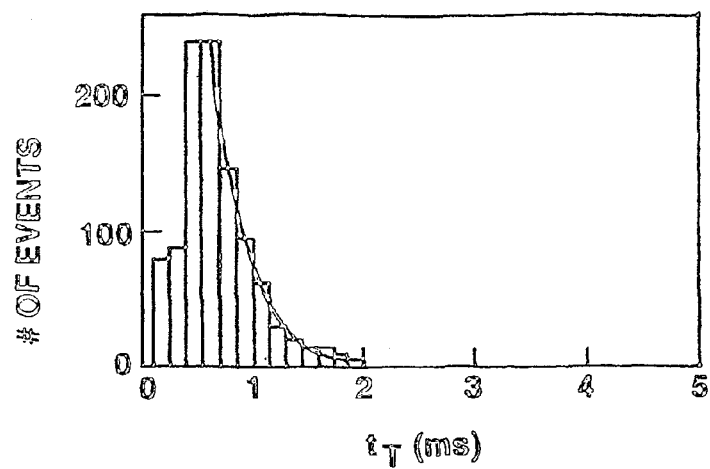
FIG. 12 is a histogram showing the translocation time distribution of a single stranded DNA (poly(dA)90 (SEQ ID NO: 18)) measured at V=120 mV and 15° C. The histogram was constructed from ~1,500 individual events. After tT>tP=0.5 ms (the most probable translocation time), the distribution is fitted by a single exponential with a time constant of 0.32 ms.

FIG. 12 displays the translocation time distribution of a single stranded DNA (poly(dA)90 (SEQ ID NO: 18)) measured at V=120 mV and 15° C. The histogram was constructed from ~1,500 individual events. The distribution of the ssDNA displays a prominent peak at $t_P$=0.5 ms, which was used to characterize the process. After tT>tP=0.5 ms (the most probable translocation time), the distribution is fitted by a single exponential with a time constant of 0.32 ms. Previous studies demonstrated that $t_P$ scales linearly with the number of bases (for 22-mers and above). Thus, from the translocation distribution of the poly(dA)$_{90}$ (SEQ ID NO: 18), it was estimated that $t_{s1}$~0.5 ms×50/90~0.28 ms. Notice that this time is much smaller than the characteristic $t_T$ of the DNA hairpin (~2-10 ms) measured in a similar way (data not shown). Nevertheless, as is described below, it is possible to decouple the initial sliding from the unzipping process, thus eliminating $t_{s1}$ completely.

The contribution of $t_{s2}$ to the unzipping process can be estimated from the studies of the translocation time of poly (dA) as a function of V. Based on these measurements estimate $t_{s2}$~660 μs at 30 mV and ~100 μs at 150 mV, for 26 nucleotides. The estimated values of $t_{s2}$ as a function of the voltage can be subtracted from the total unzipping time measured in each event to yield a more accurate estimation of $t_{unzip}$. This correction is small (see below) and did not impact the results.

The measurements of $t_{s2}$ also give an idea of the average sliding time per nucleotide (e.g., 6 μs at 100 mV). As shown below, this timescale is important for the elucidation of the unzipping mechanism inside the pore. When the hairpin is lodged in the pore its unzipping kinetics is affected by the competition between the re-zipping and sliding processes (an unzipped nucleotide can either rejoin the hairpin or slide along the channel, thereby blocking re-zipping). If the sliding time is short compared to the re-zipping time, re-zipping will be prohibited. In contrast, if the sliding time is long, the hairpin will undergo many opening-closing transitions before complete unzipping.

1. Unzipping Kinetics at Constant Force

Figure 13:
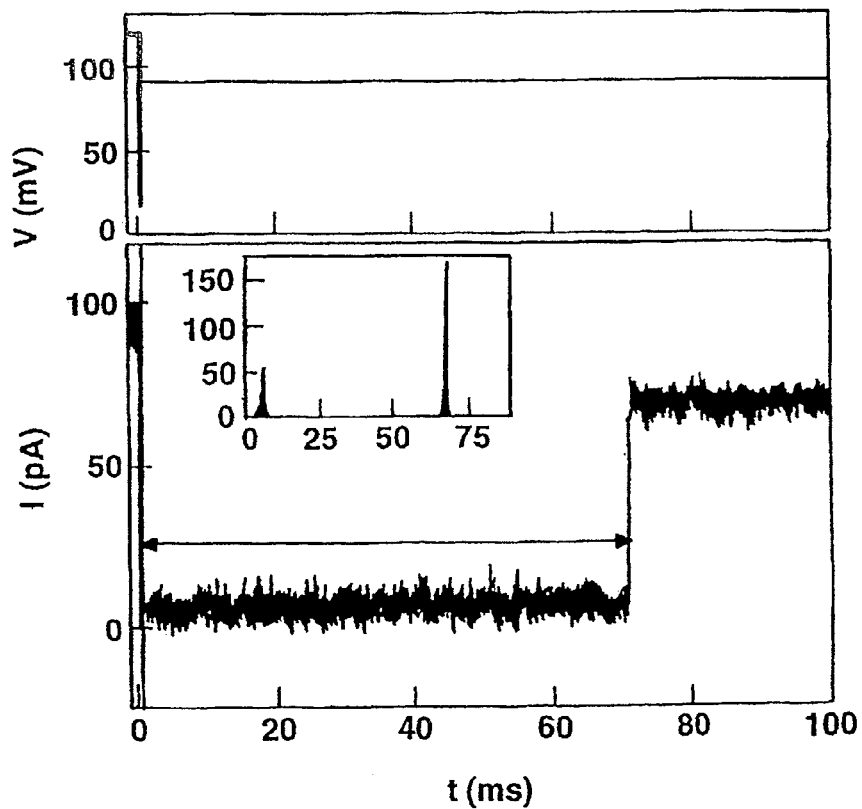
FIG. 13 is a graph showing a typical unzipping event for the constant voltage experiment. The upper panel displays the applied voltage pattern and the lower panel is the resulting pore current while the inset shows the typical distribution of the pore current measured at t=5, ms from ~1000 separate unzipping events.

The unzipping of DNA hairpins under a stationary voltage (or force) was studied. An abrupt change in the voltage was applied across the nanopore and the unzipping kinetics was measured. Typical voltage and current traces used in this experiment are shown in FIG. 13. The DNA enters the channel at time t=0. The molecule is briefly pulled and held in the pore as explained in FIG. 10. At t=0.8 ms, the unzipping voltage is applied (90 mV), but the current is blocked (lower level) until unzipping occurs at t=tU=70 ms, as indicated by the abrupt increase in the current. Upon the application of the unzipping voltage $V_U$, the current slightly increased to its proper blocked pore level (see FIG. 11 for a zoom in view of the pore current), and stayed at this blocked level until t~70 ms (measured from the application of the unzipping voltage). At this point the current abruptly increased to the open pore current level corresponding to this voltage. Since the sliding time of the unzipped hairpin is too short to be resolved on the time scale of FIG. 13, this transition signals the unzipping moment of the hairpin. The unzipping process was repeated using an automated procedure which accumulated ~100 separate unzipping events per minute.

The data was analyzed by calculating the probability that an unzipping event has occurred in the time interval [0–t], where t=0 is defined as the moment when $V_U$ is applied. For this calculation there were ~1000 unzipping events acquired and the average pore current measured in a 50 µs time window centered at time t was plotted. The distribution of the currents exhibits two well separated peaks associated with the blocked and empty pore states respectively (inset in FIG. 13). By calculating the ratio of the number of "empty pore" (high current) events to the total number of events, the accumulated unzipping probability at time t was obtained. The voltage levels used: (circles) 30 mV, (squares) 60 mV, (triangles) 90 mV, (inverted triangles) 220 mV and (diamonds) 150 mV. The measurements described above were repeated for different values of $V_U$ (30, 60, 90, 220, and 150 mV) and applied a similar analysis procedure. The data showing the probability to unzip the 11 hairpin as a function of the probing time is displayed in FIG. 14. PUNZIP was calculated as the ratio of the number of events under the high current peak to the total number of events (see inset of FIG. 13), for each probing time. At short times (i.e. t<1 ms) the unzipping probability is very small regardless of the amplitude of V. At t~10 ms there is a pronounced difference between the unzipping probabilities at small and large $V_U$ values. Because the unzipping is immediately followed by the translocation of 26 nt (single strand) through the pore, the measured unzipping time includes two terms: the true unzipping time and the sliding time ($t_{s2}$) of the 26-mer. The measurements were corrected by estimating $t_{s2}$ as explained earlier. However, because the correction is much smaller than the unzipping time (~1%), it had a very small effect on the results.

Figure 14:
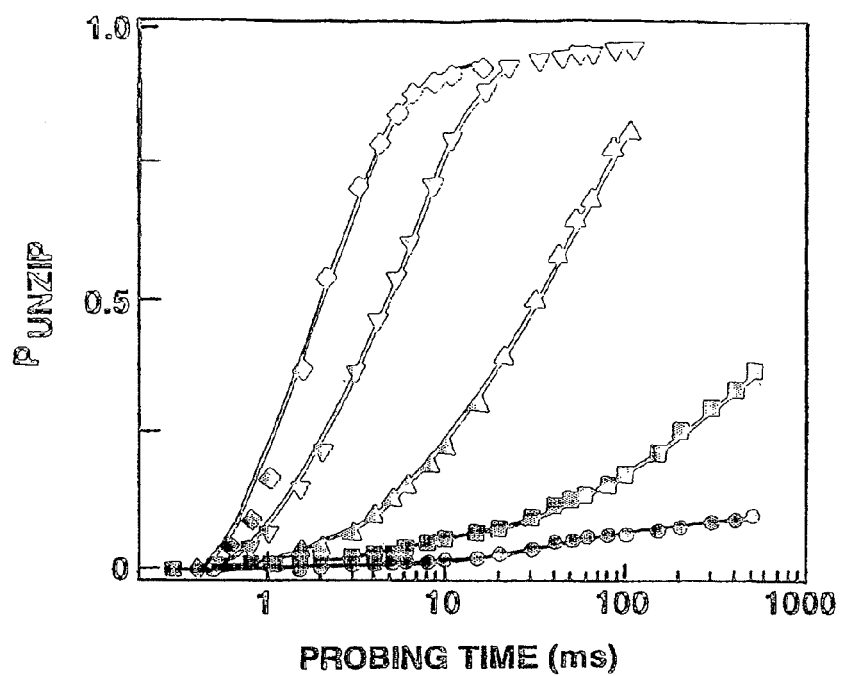
FIG. 14 is a graph showing the unzipping probability, Punzip as a function of t, for different unzipping voltage levels for HP1. The voltage levels used: (circles) 30 mV, (squares) 60 mV, (triangles) 90 mV, (inverted triangles) 120 mV and (diamonds) 150 mV.
Figure 15:
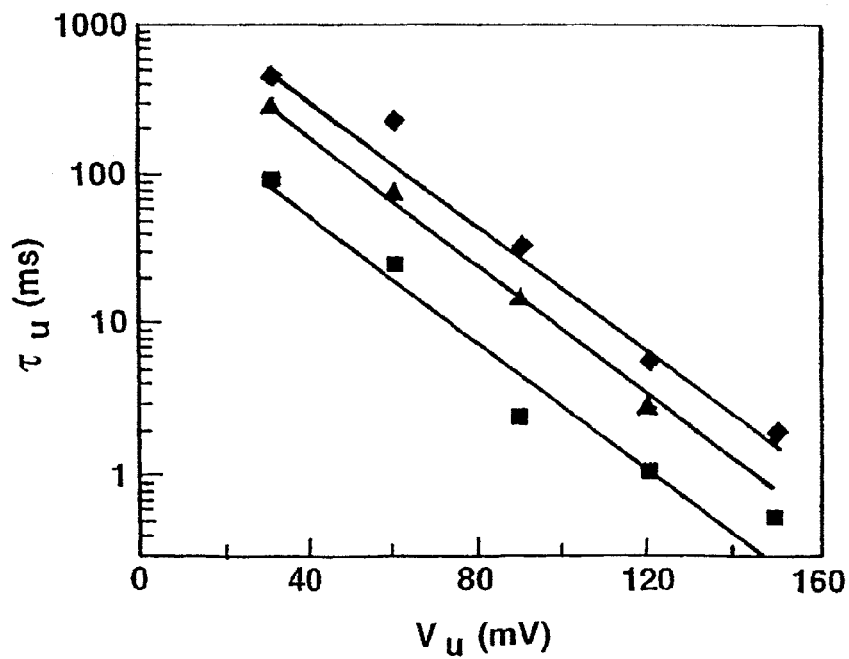
FIG. 15 is a graph plotting the dependence of $\tau_U$ on the unzipping voltage, $V_U$, is plotted in FIG. 5, for HP1 (full circles), HP2 (triangles) and HP3 (squares) The characteristic time scales obtained from the exponential fits of PUNZIP (FIG. 4) as a function of VU.

The unzipping probability distributions shown in FIG. 14, were fit by single exponential functions, which yielded the characteristic unzipping time $\tau_U$, at the different voltage levels. The dependence of $\tau_U$ on the unzipping voltage, $V_U$, is plotted in FIG. 15, for HP1 (full circles), HP2 (triangles) and HP3 (squares), respectively. It is noted that $\tau_U$ depends exponentially on $V_U$, as apparent from the straight line fits. This dependence is expected from the modified Kramers rate model: (24)$\tau_U(V_U)=\tau_0 e^{(-V_U/V_\beta)}$, where $\tau_0=Ae^{(E_b/k_B T)}$ is the zero voltage transition time, $E_b$ is the energy barrier for dissociation of the hairpin, and $V_\beta=k_B T/Q_{eff}$. The slopes of the lines in FIG. 11 give a single value of $V_\beta=22\pm2$ mV, which can be used to estimate the effective DNA charge $Q_{eff}\approx1.13\pm0.10e$. This charge is associated with roughly 22 nucleotides that span the α-HL channel and, therefore, the effective charge per nucleotide is: 1.13/12=0.094e. From the intercepts of the fits with the vertical axis, the values of $\tau_U(0)$ (at zero force) can be inferred. The experimental results showed $\tau_U(0)=2.1\pm0.2$ s for HP1, 1.2±0.1 s for HP2 and 0.34±0.05 s for HP3.

2. Unzipping Kinetics at Constant Loading Rate

With the active control method, an arbitrary time-dependent voltage V(t) can be applied to measure the dynamics of bond breakage. In particular, force spectroscopy measurements are typically performed at a constant loading rate, or ramp $\dot{V}$=dV/dt. In the following paragraphs first show the results of a derivation of the expected distribution of the unzipping voltages for any given $\dot{V}$, and the dependence of the critical voltage (or the most probable unzipping voltage) on $\dot{V}$. The analysis follows the approach of Evans and Ritchie adapted to the nanopore case. The results are consistent with this simplified model for large loading rates, but deviate from the model at lower rates. Assume an idealized 1D energy landscape along the direction of the applied force, with a single energy barrier. In equilibrium (with no force applied), the closed hairpin state is represented as a deep minimum in the energy landscape, separated from the open state by an energy barrier $E_b$. In order to unzip the hairpin, the molecule has to cross this energy barrier. In the presence of the biasing voltage (or force) the barrier is reduced and the Kramers time ($\tau_0$) is modified according to $\tau(V)=\tau_0 e^{(-V/V_\beta)}$ where $\tau_0$ and $V_\beta$ are as defined earlier. Here V=V(t) is time dependent. The probability per unit time that unzipping has occurred between t and t+dt is given by $$P(t) = \tau^{-1}(t)\exp\left(-\int_0^t \frac{dt'}{\tau(t')}\right).$$

This equation can be expressed in terms of V(t)=$\dot{V}$ t, giving the distribution of the unzipping voltages:

$$p(V) = \frac{1}{\tau_0 V \dot{Y}}\exp\left[\frac{V}{V_\beta} - \frac{V_\beta}{\tau_0 V \dot{Y}}\left(\exp\left(\frac{V}{V_\beta}\right) - 1\right)\right] \quad (1)$$

The critical unzipping voltage, $V_C$, is defined by the maximum of this distribution, which is:

$$V_c = V_\beta \ln\left[\frac{\tau_0 V \dot{Y}}{V_\beta}\right] \quad (2)$$

Figure 16:
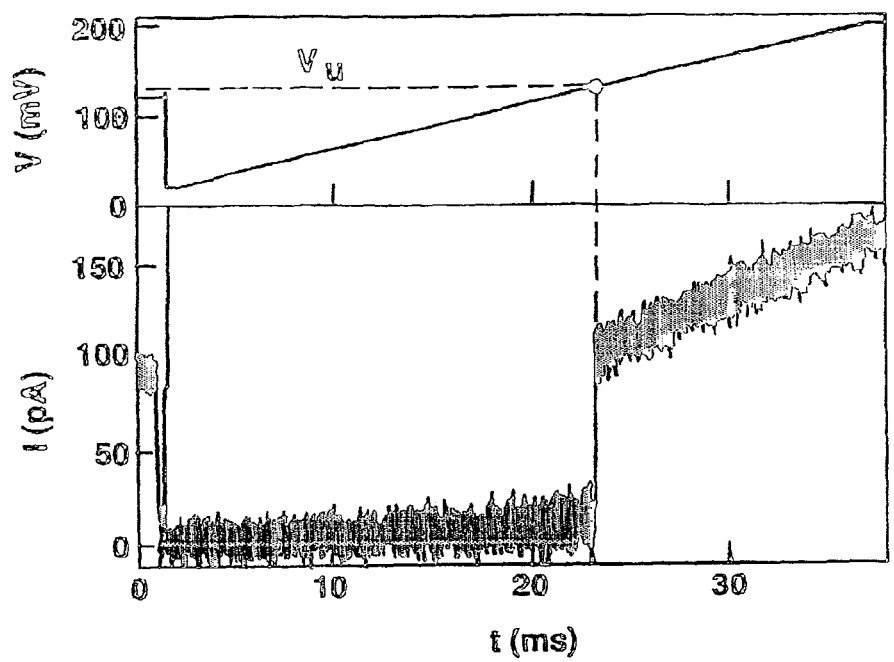
FIG. 16 is a graph showing typical unzipping event under constant loading rate, performed at a constant loading rate of 4.5 V/s where the upper panel shows voltage applied at time t=0, which represents the triggering of the DNA entry into the pore, while the lower pane shows pore current during the controlled voltage ramp.

FIG. 16 displays a typical unzipping event, performed at a constant loading rate of 4.5 V/s. The upper panel depicts the applied voltage and the lower panel shows the pore current. The unzipping is readily observable by the jump of current during the ramp of the voltage, from the blocked pore current level to the open pore current level. The unzipping voltage, VU, is directly obtained from each event. The initial entry of the DNA into the pore was performed as in the previous experiment (i.e., 0.3 ms sliding and 0.5 ms holding of the molecule inside the pore). Upon the application of the voltage ramp, the current remains at the blocked level, but at t~22 ms (measured from the beginning of the ramp), the unzipped strand rapidly slides through the pore and there is a sharp increase in the pore current. From the curve the unzipping voltage, $V_U$, (130 mV in this case) can be directly measured. The sliding time ($t_{s2}$) makes the apparent unzipping time (and thus $V_U$) slightly longer. However, as discussed above, this is a very small effect: in the case displayed here $t_{s2}$~0.12 ms and thus the correction is 0.12/22=0.005, a small fraction of the observed time.

Figure 17:
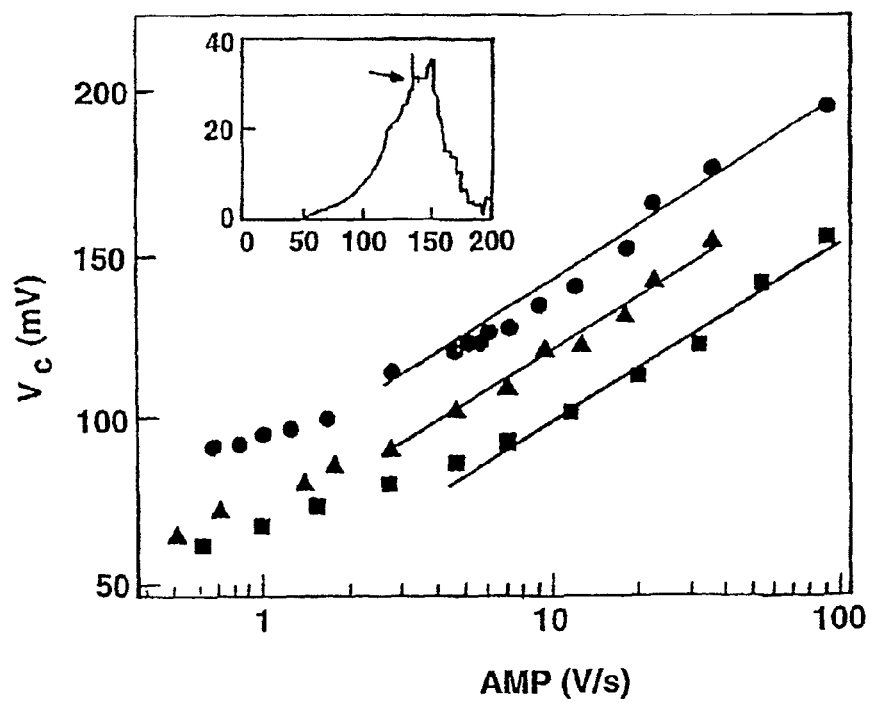
FIG. 17 is a graph showing a collection of ~1500 unzipping events (as in FIG. 6) can be used to obtain the distribution of VU and the most probable unzipping voltage VC. Main figure: a semi log plot of VC as a function of the ramp V&, for HP1 (solid circles) HP2 (triangles) and HP3 (squares).

In order to obtain sufficient statistics the unzipping experiment was repeated at least 1,000 times for any given ramp value. A typical distribution of the measured $V_U$ values is given in the inset of FIG. 17. The distribution is well approximated by Eq. 1 (solid line in the inset). The peak of the distribution is the most probable unzipping force (or the critical voltage, $V_C$). The measurements were repeated to obtain the dependence of $V_C$ on the voltage ramp in the range 0.5-100 V/s, for HP1, for the hairpin with the single mismatch, HP2 and for HP3 (7 bp helix). The data is displayed on a semi-log plot in FIG. 14 (circles, triangles and squares for HP1, HP2 and HP3 respectively). At medium and high voltage ramps (5-100 V/s), $V_C$ follows the logarithmic dependence on $\dot{V}$ predicted by Eq. 2. According to Eq. 2, the slope of the straight lines in FIG. 17 is simply $V_\beta$. From the logarithmic fit, $V_\beta$=24.7±1.0 mV for HP1, 22.5±1.1 mV for HP2, and 23.3±1.9 mV for HP3, in good agreement with the constant voltage measurements described above. As expected from the fact that $V_\beta$ depends only on the effective charge of DNA inside the pore, all the molecules yielded almost the same slope. Notice that at the lower ramp regime, the data deviates from the simple logarithmic dependence predicted by Eq. 2. This deviation is discussed below. Fitting the data (for ramp >1.6 V/s) to equation 2 yields $\tau_U(0)$=0.72 s and 0.49 s for HP1 and HP2, respectively, values that are smaller than those obtained using the constant voltage method.

Previous studies have demonstrated that the closing-opening kinetics of short blunt-ended DNA hairpins, lodged in the 2.4 nm α-HL vestibule, can be described as a single-step process, yielding time scales that correspond to jumps over energy barriers close to the calculated free enthalpies of the entire hairpin. In these experiments little or no force at all was applied to denature the molecules since the blunt-ended DNA could not enter the α-HL channel portion. In the current experiments, single stranded overhangs extending one end of the DNA hairpins were threaded inside the channel, thus biasing the hairpins' kinetics, presumably by applying force on that strand.

The active control method has allowed the extension of the unzipping measurements performed at 220 mV or above to smaller voltages, thus filling the gap between the zero force and strong force limits. At any given voltage V, there can be an estimation of the force applied on that DNA strand by $Q_{eff}V/d$ where $Q_{eff}$ is the effective charge of the ssDNA inside the channel, and d~5 nm is the channel length. Note that even at relatively small voltages (small biasing forces), the fast reannealing of thermally "melted" base-pairs can be blocked by the almost-equally fast progression of the unpaired strand inside the pore. The characteristic ssDNA sliding time was estimated from the translocation experiments. This "ratchet" mechanism can split the unzipping of the entire hairpin into several consecutive steps. Thus the 15 total unzipping time in this case is expected to be significantly shorter as compared to the zero bias kinetics.

The experiments show that the characteristic unzipping time measured at a constant force ($\tau_U$) decays exponentially with the unzipping voltage level, $V_U$. The slope of the straight lines fits and was found to be independent of the hairpin sequence (and thus their enthalpy), and allowed the estimation the effective charge on the ssDNA fragment inside the channel. The intercepts of the exponential fits to $V_U$=0 provide estimates of $\tau_U(0)$. It is interesting to compare these values with the calculated equilibrium time scales associated with fully closed to fully denatured transitions of the hairpins. The mfold server was used at 1 M Na+, to obtain $\Delta G^0$=−16.4 kcal/mole for HP1 and −12.2 kcal/mole for HP2, yielding approximated (complete closure to open) time scales of hours. In contrast, the estimate yielded $\tau_U(0)$~1 s, several orders of magnitude shorter. This difference in time scales is in line with the "ratchet" idea presented above. Specifically, if nanopore unzipping takes place through two thermally activated steps (each of ~5 bases), rather than one, the total time will be reduced to the order of seconds.

The effective charge on the ssDNA inside the 1.5 nm α-HL channel was estimated by the two independent approaches, the constant force or the fixed loading rate. Both methods yielded an effective charge of 1.13e for the strand inside the pore or 0.094e per nucleotide, indicating that the negative charge of the DNA in the channel is effectively counterbalanced by "condensation" of positively charged potassium ions and by the presence of polar groups on the inner walls of the α-HL channel, in agreement with previous results. This effective charge can be used to calculate the force at any given V.

The dynamic force measurements concur with the picture presented above. At high loading rates (ramp >2 V/s) the unzipping time (and thus $V_C$) is determined by the rapid change in the potential barrier height due to the force. In this limit the system does not undergo many opening-closing transitions and $V_C$ is directly proportional to log($\dot{V}$). For small values of $\dot{V}$ there is a soft crossover to another regime, characterized by weak dependence of the critical voltage on the loading rate. In this regime the voltage remains sufficiently low for long enough time to allow the system to fluctuate between closed and open states, before the eventual unzipping.

The slope of the logarithmic curves in FIG. 17 gives $V_\beta$ as defined in equation 2. The fit parameters are in excellent agreement with the value obtained using the constant force method. In addition, the extrapolation of the fit to $\dot{V}$=1 V/s (i.e., log($\dot{V}$)=0), can be used to estimate $\tau_U(0)$ for the two hairpins. The values obtained from the dynamic measurements are consistently smaller than the extrapolated values obtained at constant force (roughly by a factor of 2). Notice that the curves corresponding to HP1 and HP2 are displaced by roughly 20 mV. Using the measured effective charge on the DNA, this change can be translated to an energy difference of ~1 $k_B T$ (~0.6 kcal/mol).

Although the invention has been described with respect to various embodiments, it should be realized this invention is also capable of a wide variety of further and other embodiments within the spirit and scope of the appended claims.

What is claimed:

1. A composition comprising:
a polynucleotide polymer comprising a plurality of oligonucleotides joined together in a sequence corresponding to the nucleotide sequence of a target polynucleotide, wherein one or more oligonucleotides in the polynucleotide polymer correspond to one or more predetermined nucleotide bases of the target polynucleotide;
a plurality of quenchable fluorescent probes, each quenchable fluorescent probe comprising a nucleotide sequence, a fluorophore and a quencher, wherein:
each quenchable fluorescent probe is only hybridized to one of the oligonucleotides in the polynucleotide polymer; and
each of the fluorophores, except a fluorophore of one of the terminal quenchable fluorescent probes, is quenched by a quencher of an adjacent quenchable fluorescent probe.

2. The composition of claim 1, wherein the target polynucleotide is selected from the group consisting of DNA and RNA.

3. The composition of claim 2, wherein the target polynucleotide is DNA.

4. The composition of claim 3, wherein the DNA is cDNA or gDNA.

5. The composition of claim 1, wherein the nucleic acid in the quenchable fluorescent probe comprises DNA, RNA and/or PNA.

6. The composition of claim 1, wherein the oligonucleotides comprise DNA, RNA and/or PNA.

7. The composition of claim 6, wherein the oligonucleotides have a range in nucleotide bases ranging from about 5 nucleotide bases to about 20 nucleotide bases.

8. The composition of claim 1, wherein each nucleotide in the target polynucleotide is represented by a binary code of oligonucleotides.

9. The composition of claim 8, wherein the nucleotide in the target polynucleotide is selected from the group consisting of adenine, cytosine, uracil, guanine, thymine and modifications thereof.

10. The composition of claim 1, wherein the composition comprises a plurality of different quenchable fluorescent probes, each probe comprising a different fluorophore, wherein each probe is hybridized to a different oligonucleotide.

11. The composition of claim 10, wherein the composition comprises two different quenchable fluorescent probes.

12. The composition of claim 1, wherein the quenchable fluorescent probe self-quenches in isolation.

13. The composition of claim 12, wherein the quenchable fluorescent probe is a molecular beacon.

14. The composition of claim 13, wherein a portion of the nucleotide sequence on the 5' end of the molecular beacon is complementary to a portion of the nucleotide sequence on the 3' end of the molecular beacon.

15. The composition of claim 1, further comprising a nanopore system.

16. The composition of claim 15, wherein the nanopore system comprises a plurality of nanopores and one or more detection systems.

17. The composition of claim 16, wherein a nanopore in the nanopore system is selected from the group consisting of α-hemolysin, receptor for bacteriophage lambda, gramicidin, valinomycin, OmpF, OmpC, PhoE, Tsx, F-pilus, and mitochondrial porin.

18. The composition of claim 17, wherein the nanopore is α-hemolysin.

19. The composition of claim 18, wherein the α-hemolysin comprises a vestibule and a channel.

20. The composition of claim 19, wherein the vestibule is about 2.5 nm in diameter.

21. The composition of claim 20, wherein the channel has about a 1.5 nm diameter.

22. The composition of claim 21, wherein the channel has a pore size ranging from about 0.5 nm to about 2.0 nm.

23. The composition of claim 15, wherein the nanopore system comprises one or more nanopores fabricated in a polytetrafluoroethylene thin film.

24. The composition of claim 23, wherein the nanopore size is from about 0.5 nm to about 9 nm.

25. The composition of claim 15, wherein the nanopore system comprises a nanopore array.

26. The composition of claim 15, wherein the nanopore system comprises one or more channels and a lipid bilayer.

* * * * *